United States Patent [19]

Collins et al.

[11] Patent Number: 5,700,804
[45] Date of Patent: Dec. 23, 1997

[54] PHARMACEUTICAL COMPOUNDS

[75] Inventors: Mark Anthony David Collins; Maria Ines Chicarelli-Robinson; Justin Stephen Bryans, all of Berkshire, United Kingdom; Stephen James Brocchini, Highland Park, N.J.; Christopher John Latham; John Richardson Shaw, both of Berkshire, United Kingdom

[73] Assignee: Xenova Limited, United Kingdom

[21] Appl. No.: 381,932

[22] PCT Filed: Aug. 16, 1993

[86] PCT No.: PCT/GB93/01734

§ 371 Date: Apr. 11, 1995

§ 102(e) Date: Apr. 11, 1995

[87] PCT Pub. No.: WO94/04512

PCT Pub. Date: Mar. 3, 1994

[30] Foreign Application Priority Data

Aug. 14, 1992 [GB] United Kingdom ............... 9217331

[51] Int. Cl.$^6$ ....................... A61K 31/495; C07D 241/08
[52] U.S. Cl. ........................................ 514/255; 544/385
[58] Field of Search ................................ 544/385, 255

[56] References Cited

FOREIGN PATENT DOCUMENTS 621862  11/1935  Germany.
917435  2/1963  United Kingdom.

OTHER PUBLICATIONS

Chemical Abstracts, vol. 117, No. 28, 1992, Columbus, Ohio, US; abstract No. 90238v, DU Zhengming et al.
Tetrahedron, (Incl. Tetrahedron Reports) vol. 47, No. 30, 1991, Oxford G B pp. 5643–5663, Th. T. Shawe et al.
Chemical Abstracts, vol. 98, No. 28, 1983, Columbus, Ohio US; abstract No. 160674, Ian RAE et al.
Chemical Abstracts, vol. 97, No. 6, 1982, Columbus, Ohio, US; Abstract No. 40323 p. 70; Ricoh Co.
Yokoi et al, "Neihumicin, a new cytotoxic . . . ", J. Antibiotics vol. XLI No. 4 (494–501, 1988).
Shin et al, "Stereoselective systhesis . . . ", Heterocycles vol. 20 No. 7 1983, 1407–1433.
Marcuccio et al, "Pyrazine Chemistry . . . ", Aust. J. Chem 1984, 37, 1791–4.
Chem. Soc. Jpn, 59, 3917–3923 (1986), Shin et al.
Chemical Abstracts Registry printout of compounds disclosed in Du et al, Chem, Abs vol. 117, No. 28 (1992), 90238v (of record).
Bahner et al, *J. Med. Chem.* vol. 7 p. 821 (1964).
Bahner et al, *Chemical Abstracts,* vol. 62. No. 2775f (1964).
Augustin, *Chemical Abstracts,* vol. 65, No. 16969 a–f (1966).
Shin, *Kogaku Kenkyusho Shoho,* 3, pp. 9–23 (1980).
*Drug Evaluations* by American Medical Association, pp. 745–746 (1993).
Wu et al, *Chemical Abstracts,* vol. 113, No. 17408 (1990).
Kamel et al, *Journal of Antibiotics,* vol. XLIII pp. 1018–1020 (1990).
Shin et al, *J.C.S. Perkin Transactions I* pp. 419–420 (1980).
Gallina et al, *Tetrahedron 30,* pp. 667–673 (1974).

*Primary Examiner*—Emily Bernhardt
*Attorney, Agent, or Firm*—Nixon & Vanderhye

[57] ABSTRACT

Diketopiperazines of the formula:

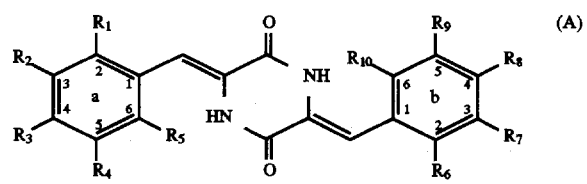

where each of $R_1$ to $R_{10}$, which may be the same or different, is independently selected from the group consisting of hydrogen, $C_1$–$C_6$ alkyl unsubstituted or substituted by one or more halogen atoms, $C_1$–$C_6$ alkoxy, $C_1$–$C_6$ alkylthio, halogen, hydroxy, nitro, phenyl, -cyano, —$CH_2OH$, —$CH_2COOH$, —$CO_2R^{11}$, —$NHCOR^{11}$, —$NHSO_2R^{13}$, —$SO_2R^{13}$, —$CON(R^{11}R^{12})$, —$SOR^{13}$, —$SO_2N(R^{11}R^{12})$, —$N(R^{11}R^{12})$, and —$O(CH_2)_nN(R^{11}R^{12})$, —$O(CH_2)_nCO_2R^{11}$, —$OCOR^{11}$, —$CH_2OCOR^{11}$, —$CH_2NHCOR^{11}$, —$CH_2NHCOOR^{13}$, —$CH_2SR^{11}$, —$CH_2SCOR^{11}$, —$CH_2S(O)_mR^{13}$ wherein m is 1 or 2, —$CH_2NHCO(CH_2)_nCO_2R^{11}$, —$N(R^{11})COR^{12}$, —$NHCOCF_3$, —$NHCO(CH_2)_nCO_2R^{11}$, —$NHCO(CH_2)_nOCOR^{11}$ and —$NHCO(CH_2)_nOR^{11}$ wherein n is 0 or is an integer of from 1 to 6, each of $R^{11}$ and $R^{12}$ is independently H or $C_1$–$C_6$ alkyl and $R^{13}$ is $C_1$–$C_6$ alkyl; or any of $R_1$ and $R_2$, $R_2$ and $R_3$, $R_3$ and $R_4$ and $R_4$ and $R_5$, or $R_6$ and $R_7$, $R_7$ and $R_8$, $R_8$ and $R_9$ and $R_9$ and $R_{10}$, form together with the carbon atoms to which they are attached a benzene ring; and pharmaceutically acceptable salts and esters thereof are inhibitors of the plasminogen activator inhibitor.

4 Claims, No Drawings

PHARMACEUTICAL COMPOUNDS

This application is a 35 USC 371 of PCT/GB93/01734 filed Aug. 6, 1993.

The present invention relates to compounds useful as inhibitors of plasminogen activator inhibitor (PAI), to their preparation and to pharmaceutical and veterinary compositions containing them.

Plasminogen activators (PAs) are serine proteases which control the activation of the zymogen, plasminogen, to the active enzyme plasmin. Plasmin is important in a number of physiological and pathological processes including fibrinolysis, tissue remodelling, tumour growth and metastasis. The glycoprotein plasminogen activator inhibitor (PAI) is an endogenous fast-acting inhibitor of PA activity. PAI is a member of the serpin family and is synthesised by a variety of cells including endothelial cells. An imbalance between PAs and PAI contributes to a number of pathological conditions including haemostasis, inflammation, tumour growth and metastasis.

The present invention provides the use of a diketopiperazine of formula (A):

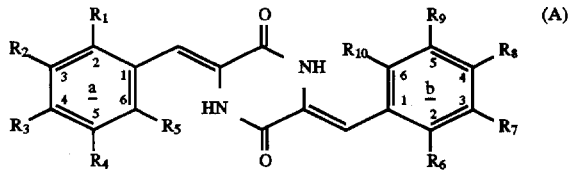

wherein each of $R_1$ to $R_{10}$, which may be the same or different, is independently selected from hydrogen, $C_1-C_6$ alkyl unsubstituted or substituted by one or more halogen atoms, $C_1-C_6$ alkoxy, $C_1-C_6$ alkylthio, halogen, hydroxy, nitro, optionally substituted phenyl, cyano, —$CH_2OH$, —$CH_2COOH$, —$CO_2R^{11}$, —$NHCOR^{11}$, —$NHSO_2R^{13}$, —$SO_2R^{13}$, —$CON(R^{11}R^{12})$, —$SOR^{13}$, —$SO_2N(R^{11}R^{12})$, —$N(R^{11}R^{12})$, —$O(CH_2)_nN(R^{11}R^{12})$, —$O(CH_2)_nCO_2R^{11}$, —$OCOR^{11}$, —$CH_2OCOR^{11}$, —$CH_2NHCOR^{11}$, —$CH_2NHCOOR^{13}$, —$CH_2SR^{11}$, —$CH_2SCOR^{11}$, —$CH_2S(O)_mR^{13}$ wherein m is 1 or 2, —$CH_2NHCO(CH_2)_nCO_2R^{11}$, —$N(R^{11})COR^{12}$, —$NHCOCF_3$, —$NHCO(CH_2)_nCO_2R^{11}$, —$NHCO(CH_2)_nOCOR^{11}$ and —$NHCO(CH_2)_nOR^{11}$ wherein n is 0 or is an integer of from 1 to 6, each of $R^{11}$ and $R^{12}$ is independently H or $C_1-C_6$ alkyl and $R^{13}$ is $C_1-C_6$ alkyl; or any of $R_1$ and $R_2$, $R_2$ and $R_3$, $R_3$ and $R_4$ and $R_4$ and $R_5$, or $R_6$ and $R_7$, $R_7$ and $R_8$, $R_8$ and $R_9$ and $R_9$ and $R_{10}$, form together with the carbon atoms to which they are attached a benzene ring which is optionally substituted; or a pharmaceutically acceptable salt or ester thereof; in the manufacture of a medicament for use as an inhibitor of plasminogen activator inhibitor.

The numerals 1 to 10 denote ring positions on the phenyl groups in formula A. The letters a and b refer to the two phenyl rings themselves.

When any two adjacent groups of $R_1$ to $R_{10}$ form, together with the carbon atoms to which they are attached, a benzene ring, that ring is either unsubstituted or it may be substituted by any of the options specified above for $R_1$ to $R_{10}$. The benzene ring forms, together with ring a or b respectively, an optionally substituted naphthalene ring structure.

When ring a or b is substituted phenyl, the benzene ring may be substituted at any of the ortho, meta and para positions by one or more substituents, for example one, two or three substituents, which may be the same or different, independently selected from the groups specified above for $R_1$ to $R_{10}$ other than hydrogen.

A $C_1-C_6$ alkyl group is typically a $C_1-C_4$ alkyl group, for example a methyl, ethyl, propyl, i-propyl, n-butyl, sec-butyl or tert-butyl group. A halogen is, for example, fluorine, chlorine, bromine or iodine. A $C_1-C_6$ alkyl group substituted by halogen may be substituted by 1, 2 or 3 halogen atoms. It may be a perhaloalkyl group, for example trifluoromethyl.

A $C_1-C_6$ alkoxy group is typically a $C_1-C_4$ alkoxy group, for example a methoxy, ethoxy, propoxy, i-propoxy, n-butoxy, sec-butoxy or tert-butoxy group. A $C_1-C_6$ alkylthio group is typically a $C_1-C_4$ alkylthio group, for example methylthio, ethylthio, propylthio, i-propylthio, n-butylthio, sec-butylthio or tert-butylthio.

In compounds of formula A free rotation may occur at room temperature about the single bonds connecting rings a and b to the double bonds at positions 3 and 6 of the piperazine-2,5-dione ring. Positions 2 and 6, and positions 3 and 5, in both rings a and b can therefore be considered as equivalent. As a consequence the following pairs of substituents can be viewed as interchangeable: $R_1$ and $R_5$; $R_2$ and $R_4$; $R_6$ and $R_{10}$; and $R_7$ and $R_9$.

Preferably one of rings a and b is unsubstituted or is mono-substituted whilst the other ring is unsubstituted or is substituted at one or more of positions 2 to 6. The ring which is mono-substituted may carry the substituent at any one of positions 2 to 6, for instance position 3 or 4, especially position 4. Thus for instance, when ring b is mono-substituted, one of $R_6$ to $R_{10}$ is other than hydrogen, preferably $R_7$ or $R_8$, especially $R_8$. When ring a is mono-substituted, one of $R_1$ to $R_5$ is other than hydrogen, preferably $R_2$ or $R_3$, especially $R_3$. When one of rings a and b is mono-substituted the substituent $R_1$ to $R_5$, or $R_6$ to $R_{10}$ respectively, is preferably selected from a halogen, for instance fluorine; an alkoxy group, for instance OMe; and an acetamido group —NHAc in which Ac denotes acetyl.

When one of rings a and b is unsubstituted, or is mono-substituted as described in the above paragraph, the other ring may bear any desired substitution pattern. For instance, the other ring may be unsubstituted or may be mono-, di- or tri-substituted at any of positions 2 to 6.

The said other ring may, for instance, be mono-substituted at any of positions 2 to 6. It may also be 2,3-, 2,4-, 2,5-, 2,6-, 3,4- or 3,5- disubstituted, or 2,3,4-, 2,3,5-, 2,3,6- or 3,4,5- trisubstituted. Thus, when the said other ring is a and is mono-substituted, four of $R_1$ to $R_5$ are hydrogen and one is other than hydrogen. When the said other ring is ring a and is disubstituted, three of $R_1$ to $R_5$ are hydrogen and two are other than hydrogen. For example $R_1$ and $R_2$, or $R_1$ and $R_3$, or $R_1$ and $R_4$, or $R_1$ and $R_5$, or $R_2$ and $R_3$, or $R_2$ and $R_4$ are other than hydrogen whilst, in each case, the other three of $R_1$ to $R_5$ are hydrogen.

When the said other ring in ring a and is trisubstituted, two of $R_1$ to $R_5$ are hydrogen and three are other than hydrogen. For example, $R_1$, $R_2$ and $R_3$, or $R_1$, $R_2$ and $R_4$, or $R_1$, $R_2$ and $R_5$, or $R_2$, $R_3$ and $R_4$ are other than hydrogen whilst, in each case, the other two of $R_1$ to $R_5$ are hydrogen.

When the said ring is b and is mono-substituted, four of $R_6$ to $R_{10}$ are hydrogen and one is other than hydrogen. When the said other ring is b and is di-substituted, three of $R_6$ to $R_{10}$ are hydrogen and two are other than hydrogen. For example $R_6$ and $R_7$, or $R_6$ and $R_8$, or $R_6$ and $R_9$, or $R_6$ and $R_{10}$, or $R_7$ and $R_8$, or $R_7$ and $R_9$, are other than hydrogen whilst, in each case, the other three of $R_6$ to $R_{10}$ are hydrogen. When the said other ring is b and is trisubstituted, two of $R_6$ to $R_{10}$ are hydrogen and three are other than hydrogen. For example $R_6$, $R_7$ and $R_8$, or $R_6$, $R_7$ and $R_9$, or $R_6$, $R_7$ and $R_{10}$, or $R_7$, $R_8$ and $R_9$ are other than hydrogen whilst, in each case, the other two of $R_6$ to $R_{10}$ are hydrogen.

Alternatively, any two adjacent substituents in the said other ring may, together with the carbon atoms to which they are attached, complete a second benzene ring which is optionally substituted, thus forming an optionally substituted naphthyl group with the said other ring. For instance, in ring a $R_1$ and $R_2$, or $R_2$ and $R_3$ may form together with carbon atoms 2 and 3, or 3 and 4 respectively, an optionally substituted benzene ring which, in turn, forms with ring a a naphthyl group which is unsubstituted or substituted by one or more groups specified above for $R_1$ to $R_{10}$. In ring b $R_6$ and $R_7$, or $R_7$ and $R_8$ may form, together with carbon atoms 2 and 3 or 3 and 4 respectively, an optionally substituted benzene ring which, in turn, forms with ring b a naphthyl group which is unsubstituted or substituted by one or more groups specified above for $R_1$ to $R_{10}$. Typically the naphthyl group in either case is unsubstituted or is monosubstituted at position 1,2,3 or 4 of the naphthalene ring structure, especially position 4. For example $R_1$ and $R_2$ together with ring a, or $R_6$ and $R_7$ with ring b, form a 4-dimethylamino-1-naphthyl group.

In a preferred series of compounds of formula A each of $R_6$ to $R_{10}$ is hydrogen. In another preferred series of compounds, one of $R_6$ to $R_{10}$ is selected from alkoxy, $NHCOR^{11}$ and halogen and the other four of $R_6$ to $R_{10}$ are H. Alkoxy may be, for instance, OMe or $OBu^n$. $NHCOR^{11}$ is typically —NHAc. Halogen is typically F or Cl. Preferably $R_8$ is alkoxy, especially OMe or $OBu^n$; $NHCOR^{11}$, especially —NHAc; or halogen, especially F or Cl; and each of $R_6$, $R_7$, $R_9$ and $R_{10}$ is H.

In the above-mentioned series of preferred compounds $R_1$ to $R_5$ are all hydrogen, or one or two of $R_1$ to $R_5$ are other than hydrogen whilst the others are hydrogen. For instance one of $R_1$, $R_2$ and $R_3$ is other than hydrogen. Alternatively $R_1$ and $R_3$, or $R_2$ and $R_3$, are other than hydrogen. Preferred values for the one or two of $R_1$ to $R_5$ which is or are other than hydrogen include alkoxy such as OMe or $OBu^n$, halogen such as Cl or F, hydroxy, $—N(R^{11}R^{12})$, $—CO_2R^{11}$, $—CH_2SCOR^{13}$, $—CH_2SR^{11}$, $—NHCOR^{11}$, $—O(CH_2)_nN(R^{11}R^{12})$, $—O(CH_2)_nCO_2R^{11}$, $—CH_2NHCO(CH_2)_nCO_2R^{11}$, $—NHCOCH_2OR^{11}$, $—NHCO(CH_2)_nOCOR^{11}$, $—CH_2NHCOOR^{13}$ and $CF_3$. It is also preferred for $R_1$ and $R_2$, $R_2$ and $R_3$, $R_3$ and $R_4$ or $R_4$ and $R_5$ to form, together with the carbon atoms to which they are attached, a benzene ring.

Particularly preferred compounds are those wherein $R_6$, $R_7$, $R_9$ and $R_{10}$ are each H, $R_8$ is selected from H, OMe and —NHAc and each of $R_1$ to $R_5$ is as specified above. In these preferred compounds $R^1$ to $R^5$ are preferably each independently selected from H, halogen, hydroxy, $C_1$-$C_6$ alkoxy, nitro, $—CH_2SCOR^{11}$, $—CH_2SR^{11}$, $—CO_2R^{11}$, $—OCOR^{13}$, $CF_3$, $—O(CH_2)_nN(R^{11}R^{12})$, $—O(CH_2)_nCO_2R^{11}$, $—CH_2NHCO(CH_2)_nCO_2R^{11}$, $—NHCO(CH_2)_nOR^{11}$, $—N(R^{11}R^{12})$, $—NHCO(CH_2)_nOCOR^{11}$, $—NHCO(CH_2)_nCO_2R^{11}$ and $—CH_2NHCO_2R^{13}$ or $R_1$ and $R_2$, $R_2$ and $R_3$, $R_3$ and $R_4$, or $R_4$ and $R_5$, form with the carbon atoms to which they are attached an optionally substituted benzene ring. Still more preferably, $R_1$ and $R_2$ are independently H, nitro or halogen, $R_3$ is H, hydroxy, $—O(CH_2)_nN(R^{11}R^{12})$, $—OCOR^{11}$, $—O(CH_2)_nCO_2R^{11}$, $—CH_2NHCO(CH_2)_nCO_2R^{11}$, $C_1$-$C_6$ alkoxy, $—NHCO(CH_2)_nOR^{11}$, $—NHCO(CH_2)_nOCOR^{11}$, $—N(R^{11}R^{12})$, $—CH_2NHCO_2R^{13}$, $—CH_2SR^{11}$ or $—NHCOR^{11}$; $R_4$ is H, halogen, $C_1$-$C_6$ alkoxy, $—CH_2SCOR^{11}$, $—CH_2SR^{11}$ or $—CO_2R^{11}$; and $R_5$ is H, nitro or halogen; or $R^2$ and $R_3$, $R_3$ and $R_4$ or $R_4$ and $R_5$ form, together with the carbon atoms to which they are attached, an optionally substituted benzene ring.

In one embodiment $R_8$ is NHAc, each of $R_6$, $R_7$, $R_9$ and $R_{10}$ is H; $R_1$ is H or halogen such as Cl or F; $R_2$ is H, $R_3$ is halogen such as F or Cl, $C_1$-$C_6$ alkoxy such as OMe, $—N(R^{11}R^{12})$ such as $NMe_2$ or $—NHCOOR^{13}$ such as $—NHCOOBu^t$; $R_4$ is H and $R_5$ is halogen such as F, Cl, Br, or is $CF_3$.

In a second embodiment $R_8$ is OMe, each of $R_6$, $R_7$, $R_9$ and $R_{10}$ is H; $R^1$ is H, nitro or halogen such as Cl; $R^2$ is H; $R_3$ is H, hydroxy, $—OCOR^{11}$ such as OAc, $—NHCO(CH_2)_nOCOR^{11}$ such as $—NHCOCH_2OAc$ or $—NHCOCH_2OR^{11}$ such as $—NHCOCH_2OH$; $R_4$ is H and $R_5$ is H or halogen such as F or Cl; or $R_2$ and $R_3$ form a benzene ring together with the carbon atoms to which they are attached.

In a third embodiment each of $R_1$, $R_6$, $R_7$, $R_8$, $R_9$ and $R_{10}$ is H; $R_2$ is H and $R_3$ is $—CH_2SR^{11}$ such as $—CH_2SMe$, $—CH_2SCOR^{11}$ such as $—CH_2SAc$, $—NHCO(CH_2)_nCO_2R^{11}$ such as $—NHCO(CH_2)_3CO_2Me$, $—O(CH_2)_nCO_2R^{11}$ such as $—O(CH_2)_4CO_2H$, $—O(CH_2)_nN(R^{11}R^{12})$ such as $—O(CH_2)_3—NMe_2$, or $—N(R^{11}R^{12})$ such as $—NMe_2$ or $R_2$ is $—CH_2SCOR^{13}$ such as $—CH_2SAc$ or $—CH_2SR^{11}$ such as $—CH_2SH$ and $R_3$ is H; and $R_4$ and $R_5$ are both H or both form, together with the carbon atoms to which they are attached, a benzene ring.

In one embodiment of the invention the compound of formula A is the following compound 3:

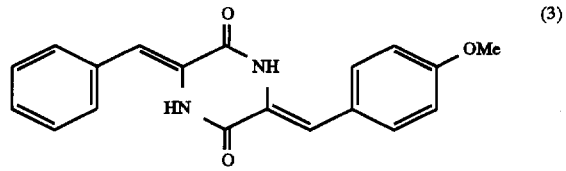

(3)

Certain diketopiperazines have been disclosed as having utility as bioactive agents. Yokoi et al in J. Antibiotics vol XLI No. 4, pp 494–501 (1988) describe structure-cytotoxicity relationship studies on a series of diketopiperazines related to neihumicin, a compound obtained from the micro-organism *Micromonospora neihuensis*. Kamei et al in J. Antibiotics vol XLIII No. 8, 1018–1020 disclose that two diketopiperazines, designated piperafizines A and B, have utility as potentiators of the cytotoxicity of vincristine.

General formula A embraces diketopiperazines which are novel. Accordingly, the present invention provides a diketopiperazine of formula (A) as defined above, or a pharmaceutically acceptable salt or ester thereof; with the exception of compounds wherein:

(i) each of $R_1$ to $R_{10}$ is H;

(ii) $R_1$ and $R_6$ are both Cl and the rest of $R_2$ to $R_{10}$ are H; $R_2$ and $R_7$ are both Cl and the rest of $R_1$ to $R_{10}$ are H; $R_3$ and $R_8$ are both Me and the rest of $R_1$ to $R_{10}$ are H; $R_2$, $R_5$, $R_7$ and $R_{10}$ are all Me and the rest of $R_1$ to $R_{10}$ are H; $R_2$, $R_3$, $R_4$, $R_7$, $R_8$ and $R_9$ are all OMe and $R_1$, $R_5$, $R_6$ and $R_{10}$ are H;

(iii) $R_8$ is OMe and the rest of $R_1$ to $R_{10}$ are H; and (iv) 3-p-nitrobenzylidene-6-benzylidene-2,5-piperazinedione and 3,6-di-p-nitrobenzylidene-2,5-piperazinedione.

Examples of specific compounds of formula A are as follows. The compound numbering is adhered to in the rest of the specification:

(3Z,6Z,)-6-benylidene-3-(4-methoxybenzylidene)-2,5-piperazinedione (compound 3)

(3Z,6Z)-6-Benzylidene-3-(2,6-dichlorobenzylidene)-2,5-piperazinedione (compound 21)

(3Z,6Z)-3-(4-Acetoxybenzylidene)-6-benzylidene-2,5-piperazinedione (compound 23)

(3Z,6Z)-6-Benzylidene-3-(4-nitrobenzylidene)-2,5-piperazinedione (compound 74)

3,6-Dibenzylidene-2,5-piperazinedione (compound 22) (mixture of isomers)

(3Z,6Z)-6-Benzylidene-3-(3-nitrobenzylidene)-2,5-piperazinedione (compound 24)

(3Z,6Z)-6-Benzylidene-3-(2-nitrobenzylidene)-2,5-piperazinedione (compound 65)
(3Z,6Z)-6-Benzylidene-3-(4-ethoxybenzylidene)-2,5-piperazinedione (compound 25)
(3Z,6Z)-6-Benzylidene-3-(4-cyanobenzylidene)-2,5-piperazinedione (compound 105)
(3Z,6Z)-3-(4-Aminobenzylidene)-6-benzylidene-2,5-piperazinedione (compound 30)
(3Z,6Z)-3-(3-Acetoxybenzylidene)-6-benzylidene-2,5-piperazinedione (compound 31)
(3Z,6Z)-3-(2-Acetoxybenzylidene)-6-benzylidene-2,5-piperazinedione (compound 32)
(3Z,6Z)-6-Benzylidene-3-(3-hydroxybenzylidene)-2,5-piperazinedione (compound 33)
(3Z,6Z)-3-(4-Acetamidobenzylidene)-6-benzylidene-2,5-piperazinedione (compound 34)
(3Z,6Z)-3-(2-Acetamidobenzylidene)-6-benzylidene-2,5-piperazinedione (compound 38)
(3Z,6Z)-3-(2-Aminobenzylidene)-6-benzylidene-2,5-piperazinedione (compound 39)
(3Z,6Z)-3-(4-Acetoxymethylbenzylidene)-6-benzylidene-2,5-piperazinedione (compound 43)
(3Z,6Z)-3-(4-Acetamidomethylbenzylidene)-6-benzylidene-2,5-piperazinedione (compound 44)
(3Z,6Z)-3,6-Dibenzylidene-2,5-piperazinedione (compound 45)
(3Z,6Z)-6-Benzylidene-3-(4-butoxybenzylidene)-2,5-piperazinedione (compound 48)
(3Z,6Z)-6-Benzylidene-3-(4-tert-butylbenzylidene)-2,5-piperazinedione (compound 51)
(3Z,6Z)-6-Benzylidene-3-(4-isopropoxybenzylidene)-2,5-piperazinedione (compound 52)
(3Z,6Z)-6-Benzylidene-3-(2,4-difluorobenzylidene)-2,5-piperazinedione (compound 54)
(3Z,6Z)-6-Benzylidene-3-(2-bromobenzylidene)-2,5-piperazinedione (compound 55)
(3Z,6Z)-6-Benzylidene-3-(4-methylthiomethylbenzylidene)-2,5-piperazinedione (compound 59)
(3Z,6Z)-6-Benzylidene-3-(3-thioacetoxymethylbenzylidene)-2,5-piperazinedione (compound 61)
3-((3Z,6Z)-6-Benzylidene-2,5-dioxopiperazin-3-ylidene)methylbenzoic acid, methyl ester (compound 62)
(3Z,6Z)-6-Benzylidene-3-(3-mercaptomethylbenzylidene)-2,5-piperazinedione (compound 64)
(3Z,6Z)-6-Benzylidene-3-(4-tert-butoxycarbonylaminobenzylidene)-2,5-piperazinedione (compound 66)
(3Z,6Z)-6-Benzylidene-3-(4-(3-N,N-dimethylaminopropoxy)benzylidene)-2,5-piperazinedione (compound 75)
(3Z,6Z)-6-Benzylidene-3-(4-thioacetoxymethylbenzylidene)-2,5-piperazinedione (compound 76)
(3Z,6Z)-6-Benzylidene-3-(2-chloro-4-hydroxybenzylidene)-2,5-piperazinedione (compound 85)
(3Z,6Z)-6-Benzylidene-3-(3,4-dimethoxybenzylidene)-2,5-piperazinedione (compound 90)
4-[(3Z,6Z)-6-Benzylidene-2,5-dioxopiperazin-3-ylidene]methylphenoxyacetic acid, methyl ester (compound 93)
4-(4-[(3Z,6Z)-6-Benzylidene-2,5-dioxopiperazin-3-ylidene]methylbenzylcarbamoyl) butanoic acid, methyl ester (compound 94)
4-(4-((3Z,6Z)-6-Benzylidene-2,5-dioxopiperazin-3-ylidene)methylbenzylcarbamoyl)pentanoic acid, methyl ester (compound 95)
5-[4-((3Z,6Z)-6-Benzylidene-2,5-dioxopiperazin-3-ylidene)methylphenoxy]pentanoic acid, methyl ester (compound 96)
5-[4-((3Z,6Z)-6-Benzylidene-2,5-dioxopiperazin-3-ylidene)methylphenoxy]pentanoic acid (compound 97)
(3Z,6Z)-6-Benzylidene-3-(4-(2-N,N-dimethylaminoethoxy)benzylidene)-2,5-piperazinedione, hydrochloride (compound 99)
(3Z,6Z)-6-Benzylidene-3-(4-(2-N,N-dimethylaminoethoxy)benzylidene)-2,5-piperazinedione (compound 102)
4-[(3Z,6Z)-6-Benzylidene-2,5-dioxopiperazin-3-ylidene]methylphenoxyacetic acid (compound 101)
(3Z,6Z)-3-(4-Acetamidobenzylidene)-6-(4-methoxybenzylidene)-2,5-piperazinedione (compound 26)
(3Z,6Z)-6-(4-Methoxybenzylidene)-3-(2-nitrobenzylidene)-2,5-piperazinedione (compound 28)
(3Z,6Z)-3-(2,6-Dichlorobenzylidene)-6-(4-methoxybenzylidene)-2,5-piperazinedione (compound 29)
(3Z,6Z)-3-(4-Hydroxybenzylidene)-6-(4-methoxybenzylidene)-2,5-piperazinedione (compound 36)
(3Z,6Z)-3-(4-Acetoxybenzylidene)-6-(4-methoxybenzylidene)-2,5-piperazinedione (compound 37)
(3Z,6Z)-3-(4-Methoxybenzylidene)-6-(4-N-methylacetamidobenzylidene)-2,5-piperazinedione (compound 41)
(3Z,6Z)-3-(4-Methoxybenzylidene)-6-(4-methylsulfonylbenzylidene)-2,5-piperazinedione (compound 46)
(3Z,6Z)-3-(4-Butoxybenzylidene)-6-(4-methoxybenzylidene)-2,5-piperazinedione (compound 47)
(3Z,6Z)-3-(4-isopropoxybenzylidene)-6-(4-methoxybenzylidene)-2,5-piperazinedione (compound 49)
(3Z,6Z)-3-(4-methoxybenzylidene)-6-(4-tert-butylbenzylidene)-2,5-piperazinedione (compound 50)
(3Z,6Z)-3-(2-Bromobenzylidene)-6-(4-methoxybenzylidene)-2,5-piperazinedione (compound 53)
(3Z,6Z)-(4-Methoxybenzylidene)-6-(4-tert-butoxycarbonylaminomethylbenzylidene)-2,5-piperazinedione (compound 56)
(3Z,6Z)-3-(4-Methoxybenzylidene)-6-(4-methylthiomethylbenzylidene)-2,5-piperazinedione (compound 57)
(3Z,6Z)-3-(4-Methoxybenzylidene)-6-(4-methylsulfonylmethylbenzylidene)-2,5-piperazinedione (compound 60)
(3Z,6Z)-3-(4-Methoxybenzylidene)-6-(3-thioacetoxymethylbenzylidene)-2,5-piperazinedione (compound 63)
(3Z,6Z)-3-(4-Aminomethylbenzylidene)-6-(4-methoxybenzylidene)-2,5-piperazinedione (compound 67)
(3Z,6Z)-3-(2,4-Difluorobenzylidene)-6-(4-methoxybenzylidene)-2,5-piperazinedione (compound 69)
(3Z,6Z)-3-(4-Methoxybenzylidene)-6-(2-trifluoromethylbenzylidene)-2,5-piperazinedione (compound 70)
(3Z,6Z)-3-(2,4-Dimethoxybenzylidene)-6-(4-methoxybenzylidene)-2,5-piperazinedione (compound 73)
4-[(3Z,6Z)-6-(4-Methoxybenzylidene)-2,5-dioxopiperazin-3-ylidene]methylbenzamide (compound 80)
(3Z,6Z)-3-(4-Methoxybenzylidene)-6-(4-trimethylacetoxybenzylidene)-2,5-piperazinedione (compound 81)

(3Z,6Z)-3-(4-Methoxybenzylidene)-6-(4-methoxycarbonylaminobenzylidene)-2,5-piperazinedione (compound 83)

(3Z,6Z)-3-(2-Chloro-4-hydroxybenzylidene)-6-(4-methoxybenzylidene)-2,5-piperazinedione (compound 84)

(3Z,6Z)-3-(4-Acetoxyacetylaminobenzylidene)-6-(4-methoxybenzylidene)-2,5-piperazinedione (compound 87)

(3Z,6Z)-3-(3,4-Dimethoxybenzylidene)-6-(4-methoxybenzylidene)-2,5-piperazinedione (compound 91)

4-((3Z,6Z)-6-(4-Methoxybenzylidene)-2,5-dioxopiperazin-3-ylidene)-4-methylbenzylcarbamoyl)butanoic acid, methyl ester (compound 100)

(3Z,6Z)-3-(4-Methoxybenzylidene)-6-(2-naphthylmethylene)-2,5-piperazinedione (compound 27)

(3Z,6Z)-3-(4-Hydroxyacetylaminobenzylidene)-6-(4-methoxybenzylidene)-2,5-piperazinedione (compound 88)

(3Z,6Z)-3-(4-Acetamidobenzylidene)-6-benzylidene-2,5-piperazinedione (compound 34)

(3Z,6Z)-3,6-Di-(3-Nitrobenzylidene)-2,5-piperazinedione (compound 35)

(3Z,6Z)-3-(4-Acetamidobenzylidene)-6-(2,6-dichlorobenzylidene)-2,5-piperazinedione (compound 40)

(3Z,6Z)-3-(4-Acetamidobenzylidene)-6-(4-chlorobenzylidene)-2,5-piperazinedione (compound 42)

(3Z,6Z)-3-(4-Acetamidobenzylidene)-6-(4-acetoxymethylbenzylidene)-2,5-piperazinedione (compound 58)

(3Z,6Z)-3-(4-Acetamidobenzylidene)-6-(2-fluorobenzylidene)-2,5-piperazinedione (compound 71)

(3Z,6Z)-3-(4-Acetamidobenzylidene)-6-(4-fluorobenzylidene)-2,5-piperazinedione (compound 72)

(3Z,6Z)-6-(Benzylidene)-3-(2,4-difluorobenzylidene)-2,5-piperazinedione (compound 76)

(3Z,6Z)-6-(4-Acetamidobenzylidene)-3-(2-trifluoromethylbenzylidene)-2,5-piperazinedione (compound 78)

(3Z,6Z)-6-(4-Acetamidobenzylidene)-3-(2-bromobenzylidene)-2,5-piperazinedione (compound 79)

(3Z,6Z)-3-(4-Acetamidobenzylidene)-6-(4-trimethylacetoxybenzylidene)-2,5-piperazinedione (compound 82)

(3Z,6Z)-3-(4-Acetamidobenzylidene)-6-(4-dimethylaminobenzylidene)-2,5-piperazinedione (compound 86)

(3Z,6Z)-3-(4-Acetamidobenzylidene)-6-(4-tert-butoxycarbonylaminomethylbenzylidene)-2,5-piperazinedione (compound 68)

Compounds of formula A, both known and novel, may be prepared by a process which comprises either (i) condensing compound of formula (I)

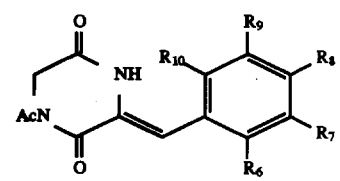

wherein $R_6$ to $R_{10}$ are as defined above and are optionally protected, with a compound of formula (II):

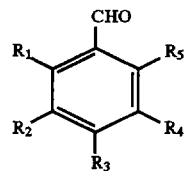

wherein $R_1$ to $R_5$ are defined above and are optionally protected, in the presence of a base in an organic solvent; or (ii) condensing a compound of formula (I'):

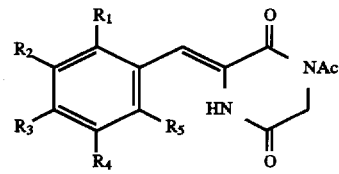

wherein $R_1$ to $R_5$ are as defined above and are optionally protected, with a compound of formula (III):

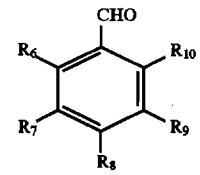

wherein $R_6$ to $R_{10}$ are as defined above and are optionally protected, in the presence of a base in an organic solvent; and, in either case (i) or (ii), if required, removing optionally present protecting groups and/or, if desired, converting one compound of formula A into another compound of formula A, and/or, if desired, converting a compound of formula A into a pharmaceutically acceptable salt or ester thereof, and/or, if desired, converting a salt or ester into a free compound, and/or, if desired, separating a mixture of isomers of compounds of formula A into the single isomers.

A compound of formula A produced directly by the condensation reaction between (I) and (II) or (I') and (III) may be modified, if desired, by converting one or more of groups $R_1$ to $R_{10}$ into different groups $R_1$ to $R_{10}$. These optional conversions may be carried out by methods known in themselves. For example, a compound of formula A in which one or more of $R_1$ to $R_{10}$ is an ester group may be converted to a compound of formula A wherein the corresponding substituent is a free —COOH group, by acid or alkaline hydrolysis at a suitable temperature, for example from ambient temperature to 100° C.

A compound of formula A in which one or more of $R_1$ to $R_{10}$ is a —$CO_2H$ group may be converted into a compound of formula A wherein the corresponding substituent is esterified by esterification, for example by treating the carboxylic acid with a suitable $C_1$-$C_6$ alkyl alcohol in the presence of 1,3-dicyclohexylcarbodiimide in an inert solvent.

A compound of formula A in which one or more of $R_1$ to $R_{10}$ is a free —$CO_2H$ group may be converted into a compound of formula A in which the corresponding substituent is a group —$CON(R^{11}R^{12})$, wherein $R^{11}$ and R are as defined above, for example by treatment with ammonia or an amine in the presence of 1,3-dicyclohexylcarbodiimide in an inert solvent.

A compound of formula A in which one or more of $R_1$ to $R_{10}$ is a free —$CO_2H$ group may be converted into a compound of formula A wherein the corresponding substituent is a —$CH_2OH$ group by reduction, for example using borane in a suitable solvent such as tetrahydrofuran.

A compound of formula A in which one or more of $R_1$ to $R_{10}$ is a nitro group may be converted into a compound of formula A in which the corresponding substituent is an amino group by reduction under standard conditions, for example by catalytic hydrogenation.

Protecting groups for $R_1$ to $R_{10}$ in any of the compounds of formulae (I), (I'), (II) and (III) are optionally introduced prior to step (i) or step (ii) when any of groups $R_1$ to $R_{10}$ are groups which are sensitive to the condensation reaction conditions or incompatible with the condensation reaction, for example a —COOH, —CH$_2$OH or amino group. The protecting groups are then removed at the end of the process. Any conventional protecting group suitable for the group $R_1$ to $R_{10}$ in question may be employed, and may be introduced and subsequently removed by well-known standard methods.

The condensation reaction between compounds (I) and (II) or (I') and (III) is suitably performed in the presence of a base which is potassium t-butoxide, sodium hydride, potassium carbonate, sodium carbonate, caesium carbonate, sodium acetate, potassium fluoride on alumina, or triethylamine in a solvent such as dimethylformamide, or in the presence of potassium t-butoxide in t-butanol or a mixture of t-butanol and dimethylformamide. The reaction is typically performed at a temperature from 0° C. to the reflux temperature of the solvent.

The compounds of formula (I) may be prepared by a process comprising reacting 1,4-diacetyl-2,5-piperazinedione with a compound of formula (III) as defined above, in the presence of a base in an organic solvent. Similarly, the compounds of formula (I') may be prepared by a process which comprises reacting 1,4-diacetyl-2,5-piperazinedione with a compound of formula (II) as defined above, in the presence of a base in an organic solvent.

If necessary, the resulting compound of formula (I) or (I') can be separated from other reaction products by chromatography.

The reaction of 1,4-diacetyl-2,5-piperazinedione with the compound of formula (III) or (II) is suitably performed under the same conditions as described above for the condensation between compounds (I) and (II), or (I') and (III).

The substituted benzaldehydes of formulae (II) and (III) are known compounds or can be prepared from readily available starting materials by conventional methods. The 1,4-diacetyl-2,5-piperazinedione used as a starting material in the preparation of compounds of formula (I) may be prepared by treating 2,5-piperazinedione (glycine anhydride) with an acetylating agent. The acetylation may be performed using any conventional acetylating agent, for example acetic anhydride under reflux or, alternatively, acetic anhydride at a temperature below reflux in the presence of 4-dimethylaminopyridine.

Compounds of formula (I) may also be prepared by the microwave irradiation of a mixture comprising 1,4-diacetyl-2,5-piperazinedione, a compound of formula (III) and potassium fluoride on alumina (as base) in the absence of solvent.

Compounds of formula (I) may alternatively be prepared directly from 2,5-piperazinedione (glycine anhydride) by a process which comprises treating the 2,5-piperazinedione with a mixture comprising a compound of formula (III), sodium acetate and acetic anhydride at an elevated temperature, for example under reflux.

Compounds of formula (I') may be prepared by analogous processes, replacing compound (III) in each case by a compound of formula (II).

Compounds of formula A may also be prepared by a process comprising the microwave irradiation of (i) a mixture comprising a compound of formula (I) as defined above, a compound of formula (II) and potassium fluoride on alumina, or (ii) a mixture comprising a compound of formula (I') a compound of formula (III) and potassium fluoride on alumina, or (iii) a mixture comprising 1,4-diacetyl-2,5-piperazinedione, a compound of formula (II), a compound of formula (III) and potassium fluoride on alumina. The irradiation is performed in the absence of a solvent.

Compounds of formula (A) may also be obtained directly by a process which comprises condensing together 1,4-diacetyl-2,5-piperazinedione, a compound of formula (II) and a compound of formula (III) in the presence of a base in an organic solvent. Suitable bases, solvents and reaction conditions are as described above for the condensation reaction between, for example, compounds (I) and (II).

An alternative direct process for the preparation of compounds of formula (A) comprises condensing together 2,5-piperazinedione, a compound of formula (II) and a compound of formula (III) in the presence of sodium acetate and acetic anhydride at elevated temperature, for example under reflux.

An alternative process for the preparation of compounds of formula (I) comprises treating a compound of formula (V):

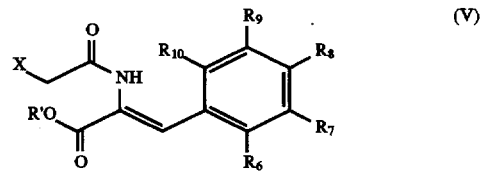

wherein $R_6$ to $R_{10}$ are as defined above, X is a halogen and R' is a $C_1$–$C_6$ alkyl group, with ammonia followed by acetic anhydride.

Compounds of formula (I') may be prepared by an analogous process which comprises treating a compound of formula (V'):

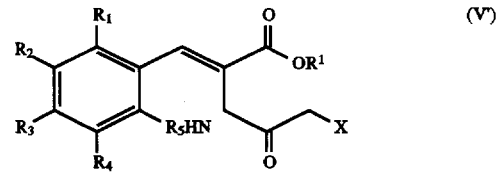

wherein $R_1$ to $R_5$, X and $R^1$ are as defined above, with ammonia followed by acetic anhydride.

X in formula (V) or (V') is typically iodine. $R^1$ is, for example, a $C_1$–$C_4$ alkyl group such as a methyl, ethyl, propyl, i-propyl, butyl, sec-butyl or tert-butyl group.

A review of synthetic approaches to unsaturated 3-monosubstituted and 3,6-disubstituted-2,5-piperazinediones is provided in Heterocycles, 1983, 20, 1407 (C. Shin).

Compounds of formula (A) may be converted into pharmaceutically acceptable salts, and salts may be converted into the free compound, by conventional methods. Suitable salts include salts with pharmaceutically acceptable, inorganic or organic, bases. Examples of inorganic bases include ammonia and carbonates, hydroxides and hydrogen carbonates of group I and group II metals such as sodium, potassium, magnesium and calcium. Examples of organic bases include aliphatic and aromatic amines such as methylamine, triethylamine, benzylamine, dibenzylamine or α- or β-phenylethylamine, and heterocyclic bases such as piperidine, 1-methylpiperidine and morpholine.

Compounds of formula (A) may also be converted into pharmaceutically acceptable esters. Suitable esters include branched or unbranched, saturated or unsaturated $C_1$–$C_6$ alkyl esters, for example methyl, ethyl and vinyl esters.

Preferred compounds of formula A are depicted by means of their substitution patterns in Table 1 which follows. The compound numbering is adhered to in the rest of the specification. Characterising data for the compounds are set out in Table 2 in Example 16.

TABLE 1

| COMPOUND NO. | $R_1$ | $R_2$ | $R_3$ | $R_4$ | $R_5$ | $R_6$ | $R_7$ | $R_8$ | $R_9$ | $R_{10}$ | PREPARED IN EXAMPLE |
|---|---|---|---|---|---|---|---|---|---|---|---|
| 21 | Cl | H | H | H | Cl | H | H | H | H | H | 5 |
| 22 | H | H | H | H | H | H | H | H | H | H | 10 |
| 23 | H | H | OAc | H | H | H | H | H | H | H | 6 |
| 24 | H | $NO_2$ | H | H | H | H | H | H | H | H | 6 |
| 25 | H | H | OEt | H | H | H | H | H | H | H | 5 |
| 26 | H | H | NHAc | H | H | H | H | OMe | H | H | 7 |
| 27 | H | - Benzene - | | H | H | H | H | OMe | H | H | 14 |
| 28 | $NO_2$ | H | H | H | H | H | H | OMe | H | H | 8 |
| 29 | Cl | H | H | H | Cl | H | H | OMe | H | H | 7 |
| 30 | H | H | $NH_2$ | H | H | H | H | H | H | H | 13 |
| 31 | H | OAc | H | H | H | H | H | H | H | H | 6 |
| 32 | OAc | H | H | H | H | H | H | H | H | H | 6 |
| 33 | H | OH | H | H | H | H | H | H | H | H | 13 |
| 34 | H | H | NHAc | H | H | H | H | H | H | H | 5 |
| 35 | H | $NO_2$ | H | H | H | H | $NO_2$ | H | H | H | 11 |
| 36 | H | H | OH | H | H | H | H | OMe | H | H | 13 |
| 37 | H | H | OAc | H | H | H | H | OMe | H | H | 7 |
| 38 | NHAc | H | H | H | H | H | H | H | H | H | 5 |
| 39 | $NH_2$ | H | H | H | H | H | H | H | H | H | 13 |
| 40 | H | H | NHAc | H | H | Cl | H | H | H | Cl | 9 |
| 41 | H | H | NMeAc | H | H | H | H | OMe | H | H | 7 |
| 42 | H | H | Cl | H | H | H | H | NHAc | H | H | 9 |
| 43 | H | H | $CH_2OAc$ | H | H | H | H | H | H | H | 5 |
| 44 | H | H | $CH_2NHAc$ | H | H | H | H | H | H | H | 5 |
| 45 | H | H | H | H | H | H | H | H | H | H | 5 |
| 46 | H | H | $SO_2Me$ | H | H | H | H | OMe | H | H | 7 |
| 47 | H | H | OBu$^n$ | H | H | H | H | OMe | H | H | 7 |
| 48 | H | H | OBu$^n$ | H | H | H | H | H | H | H | 5 |
| 49 | H | H | OPr$^i$ | H | H | H | H | OMe | H | H | 7 |
| 50 | H | H | Bu$^t$ | H | H | H | H | OMe | H | H | 7 |
| 51 | H | H | Bu$^t$ | H | H | H | H | H | H | H | 5 |
| 52 | H | H | OPr$^i$ | H | H | H | H | H | H | H | 5 |
| 53 | Br | H | H | H | H | H | H | OMe | H | H | 7 |
| 54 | F | H | F | H | H | H | H | H | H | H | 5 |
| 55 | Br | H | H | H | H | H | H | H | H | H | 5 |
| 56 | H | H | $CH_2NHBOC$ | H | H | H | H | OMe | H | H | 7 |
| 57 | H | H | OMe | H | H | H | H | $CH_2SMe$ | H | H | 7 |
| 58 | H | H | NHAc | H | H | H | H | $CH_2OAc$ | H | H | 9 |
| 59 | H | H | H | H | H | H | H | $CH_2SMe$ | H | H | 5 |
| 60 | H | H | OMe | H | H | H | H | $CH_2SO_2Me$ | H | H | 7 |
| 61 | H | $CH_2SAc$ | H | H | H | H | H | H | H | H | 5 |
| 62 | H | $CO_2Me$ | H | H | H | H | H | H | H | H | 5 |
| 63 | H | $CH_2SAc$ | H | H | H | H | H | OMe | H | H | 7 |
| 64 | H | $CH_2SH$ | H | H | H | H | H | H | H | H | 13 |
| 65 | $NO_2$ | H | H | H | H | H | H | H | H | H | 6 |
| 66 | H | H | $CH_2NHBOC$ | H | H | H | H | H | H | H | 5 |
| 67 | H | H | $CH_2NH_2$ | H | H | H | H | OMe | H | H | 13 |
| 68 | H | H | $CH_2NHBOC$ | H | H | H | H | NHAc | H | H | 9 |
| 69 | F | H | F | H | H | H | H | OMe | H | H | 7 |
| 70 | $CF_3$ | H | H | H | H | H | H | OMe | H | H | 7 |
| 71 | F | H | H | H | H | H | H | NHAc | H | H | 9 |
| 72 | H | H | F | H | H | H | H | NHAc | H | H | 9 |
| 73 | OMe | H | OMe | H | H | H | H | OMe | H | H | 7 |
| 74 | H | H | $NO_2$ | H | H | H | H | H | H | H | 6 |
| 75 | H | H | H | H | H | H | H | $O(CH_2)_3NMe_2$ | H | H | 5 |
| 76 | H | H | H | H | H | H | H | $CH_2SAc$ | H | H | 5 |
| 77 | F | H | F | H | H | H | H | NHAc | H | H | 9 |
| 78 | $CF_3$ | H | H | H | H | H | H | NHAc | H | H | 9 |
| 79 | Br | H | H | H | H | H | H | NHAc | H | H | 9 |
| 80 | H | H | OMe | H | H | H | H | $CONH_2$ | H | H | 7 |
| 81 | H | H | OMe | H | H | H | H | OCOBu$^t$ | H | H | 7 |

TABLE 1-continued

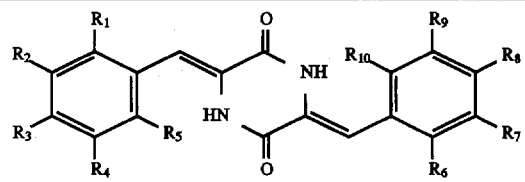

| COMPOUND NO. | R₁ | R₂ | R₃ | R₄ | R₅ | R₆ | R₇ | R₈ | R₉ | R₁₀ | PREPARED IN EXAMPLE |
|---|---|---|---|---|---|---|---|---|---|---|---|
| 82 | H | H | NHAc | H | H | H | H | OCOBuᵗ | H | H | 9 |
| 83 | H | H | NHCOOMe | H | H | H | H | OMe | H | H | 7 |
| 84 | Cl | H | OH | H | H | H | H | OMe | H | H | 7 |
| 85 | Cl | H | OH | H | H | H | H | H | H | H | 5 |
| 86 | H | H | NHAc | H | H | H | H | NMe₂ | H | H | 12 |
| 87 | H | H | NHCOCH₂OAc | H | H | H | H | OMe | H | H | 7 |
| 88 | H | H | NHCOCH₂OH | H | H | H | H | OMe | H | H | 13 |
| 89 | H | H | H | H | H | -Benzene- | | NMe₂ | H | H | 5 |
| 90 | H | OMe | OMe | H | H | H | H | H | H | H | 5 |
| 91 | H | OMe | OMe | H | H | H | H | OMe | H | H | 7 |
| 92 | H | OMe | OMe | H | H | H | H | NHAc | H | H | 9 |
| 93 | H | H | OCH₂CO₂Me | H | H | H | H | H | H | H | 5 |
| 94 | H | H | CH₂NHCO(CH₂)₃CO₂Me | H | H | H | H | H | H | H | 5 |
| 95 | H | H | CH₂NHCO(CH₂)₄CO₂Et | H | H | H | H | H | H | H | 5 |
| 96 | H | H | O(CH₂)₄CO₂Me | H | H | H | H | H | H | H | 5 |
| 97 | H | H | O(CH₂)₄CO₂H | H | H | H | H | H | H | H | 13 |
| 98 | H | H | O(CH₂)₃NMe₂.HCl | H | H | H | H | H | H | H | 15 |
| 99 | H | H | O(CH₂)₂NMe₂.HCl | H | H | H | H | H | H | H | 15 |
| 100 | H | H | CH₂NHCO(CH₂)₃CO₂Me | H | H | H | H | OMe | H | H | 7 |
| 101 | H | H | OCH₂CO₂H | H | H | H | H | H | H | H | 13 |
| 102 | H | H | O(CH₂)₂NMe₂ | H | H | H | H | H | H | H | 5 |
| 103 | F | H | H | H | H | H | H | OMe | H | H | 7 |
| 104 | H | H | CH₂OH | H | H | H | H | NHAc | H | H | 13 |
| 105 | H | H | H | H | H | H | H | CN | H | H | 6 |

The diketopiperazines of formula (A), both novel and known and their pharmaceutically acceptable salts and esters (referred to hereinafter as the "present compounds") have utility as inhibitors of PAI. Elevated levels of PAI-1, by reducing the net endogenous fibrinolytic capacity, can contribute to the pathogenesis of various thrombotic disorders including myocardial infarction, deep vein thrombosis and disseminated intravascular coagulation. The present compounds therefore can act as inhibitors of the tPA/PAI-1 interaction. The present compounds can be used in the treatment of haemostatic disorders. A human or animal, e.g. a mammal, can therefore be treated by a method comprising administration of a therapeutically effective amount of a diketopiperazine of formula (A) or a pharmaceutically or veterinarily acceptable salt thereof.

Tissue plasminogen activator (tPA) is used as a fibrinolytic agent in the treatment of thrombotic disorders. The efficacy of the tPA in this role may be enhanced if it is administered together with a PAI inhibitor. A human or animal, e.g. a mammal, can therefore be treated by a method comprising the combined administration of a therapeutically effective amount of tPA and a therapeutically effective amount of any one of the present compounds. The present invention also provides products containing a diketopiperazine of formula (A) or a pharmaceutically acceptable salt or ester thereof and tPA as a combined preparation for simultaneous, separate or sequential use in the treatment of thrombotic disorders, for example where there is inappropriate PAI activity. In such products the present compound is formulated for oral or parenteral (intravenous, intramuscular or subcutaneous) administration and the tPA is formulated for intravenous administration.

As one example, during acute myocardial infarction (MI) one of the present compounds may be administered to a patient together with tPA to enhance the efficacy of the tPA treatment. As a further example, early re-occlusion following treatment of a patient with tPA may be prevented by the post-MI administration of one of the present compounds.

The compounds of formula (A) have been tested in a PAI functional assay. In this assay, a compound is incubated with PAI-1 prior to addition to the tPA assay system. Inhibition of PAI-1 results in the production of plasmin from plasminogen. In turn, plasmin cleaves the chromogenic substrate S2251 (Kabi Vitrum) producing pNA (p-nitroaniline) which is detected spectrophotometrically at 405 nm (K. Nilsson et al, Fibrinolysis (1987) 1, 163–168). The results of the assay are reported in Example 1 which follows.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 10 mg/kg, most commonly in the range of 0.01 to 5 mg/kg, body weight. Such a dosage may be given, for example, from 1 to 5 times daily by bolus infusion, infusion over several hours and/or repeated administration.

When one of the present compounds is administered in combination with tPA to adult humans, the dosage adopted for each route of administration is typically from 0.001 to 10 mg, more typically 0.01 to 5 mg per kg body weight for a compound of the invention and from 5 to 500 mg administered intravenously for the tPA. A suitable dosage regimen for the tPA is 100 mg given intravenously over 3 hours as follows: 10% of the total dose as an i.v. bolus over 1–2 minutes, 50% of the total dose as an infusion over 1 hour, 40% of the total dose as an infusion over the subsequent 2 hours.

A diketopiperazine of formula (A) or a pharmaceutically acceptable salt or ester thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as an inhibitor of PAI comprising any one of the present compounds is therefore provided.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Some of the present compounds are insoluble in water. A compound may be encapsulated within liposomes.

The following Examples illustrate the invention:

EXAMPLE 1

TESTING OF THE PRESENT COMPOUNDS AS PAI INHIBITORS

Compounds of formula (A) were tested in a PAI chromogenic substrate assay. In the first assay (K. Nilsson, Fibrinolysis (1987) 1, 163–168) each compound was incubated with PAI-1 prior to addition to the tPA assay system. Inhibition of PAI-1 by the compound of formula (Aa) resulted in the production of plasmin from plasminogen. In turn, the plasmin cleaved the chromogenic substrate S2251 (Kabi-Vitrum) producing pNA (p-nitroaniline) which was detected spectrophotometrically at 405 nm.

The degrees of inhibition observed in the chromogenic substrate assay at various concentrations of compounds of formula (A) are presented in Table 3.

TABLE 3

INHIBITION OF PAI-1 IN THE FIRST S2251 CHROMOGENIC SUBSTRATE ASSAY

| Compound No. | Concentration in µm | | | | |
|---|---|---|---|---|---|
| | 100 | 50 | 25 | 12.5 | 6.25 |
| 21 | 79 | 35 | 2 | 0 | 0 |
| 22 | 61 | 2 | 1 | 0 | 0 |
| 25 | 52 | 25 | 1 | 0 | 0 |
| 27 | 70 | 35 | 8 | 9 | |
| 28 | 71 | 74 | 45 | 1 | 0 |
| 29 | 80 | 76 | 34 | 1 | 0 |
| 30 | 66 | 23 | 5 | 2 | |
| 31 | 58 | 12 | 2 | 1 | 0 |
| 32 | 87 | 36 | 3 | 1 | 0 |
| 33 | 56 | 3 | 1 | 1 | 0 |
| 35 | 52 | 28 | 2 | | |
| 36 | 71 | 6 | 1 | | |
| 37 | 69 | 19 | 2 | | |
| 38 | 64 | 3 | 1 | 1 | 1 |
| 39 | 67 | 20 | 1 | 1 | 0 |
| 40 | 61 | 61 | 23 | 4 | 1 |
| 41 | 51 | 45 | 32 | 8 | 3 |
| 43 | 59 | 45 | 3 | 1 | 1 |
| 44 | 51 | 2 | 1 | 1 | 1 |
| 45 | 53 | 13 | 1 | 1 | |
| 46 | 39 | 42 | 38 | 14 | |
| 47 | 75 | 58 | 14 | 14 | |
| 48 | 73 | 57 | 26 | 3 | |
| 49 | 60 | 47 | 8 | 1 | |
| 50 | 62 | 37 | 22 | 2 | |
| 51 | 79 | 61 | 38 | 5 | |
| 52 | 68 | 45 | 15 | 2 | |
| 53 | 55 | 32 | 9 | 2 | |
| 54 | 50 | 0 | 1 | 0 | |
| 55 | 65 | 43 | 11 | 1 | |
| 56 | 82 | 60 | 15 | 2 | |
| 57 | 82 | 72 | 38 | 2 | |
| 58 | 60 | 31 | 1 | 1 | |
| 59 | 71 | 76 | 60 | 19 | |
| 60 | 62 | 52 | 25 | 1 | |
| 61 | 83 | 88 | 69 | 26 | |
| 62 | 83 | 33 | 13 | 36 | |
| 63 | 69 | 70 | 44 | 36 | |
| 66 | 85 | 70 | 46 | 2 | |
| 67 | 53 | 60 | 46 | 2 | |
| 68 | 63 | 89 | 67 | 37 | |
| 69 | 68 | 40 | 14 | 3 | |
| 70 | 94 | 78 | 21 | 4 | |
| 73 | 50 | 3 | 1 | 2 | |
| 75 | 59 | 52 | 33 | 6 | 2 |
| 76 | 66 | 75 | 50 | 5 | 2 |
| 77 | 33 | 66 | 80 | 61 | 1 |
| 78 | 30 | 57 | 36 | 4 | 2 |
| 79 | 42 | 55 | 27 | 2 | 1 |
| 80 | 53 | 9 | 1 | 0 | |
| 81 | 64 | 1 | 1 | 0 | |
| 82 | 80 | 3 | 1 | 1 | |
| 83 | 56 | 1 | 1 | 1 | |
| 84 | 52 | 38 | 10 | 2 | 1 |
| 85 | 35 | 49 | 43 | 27 | 13 |
| 86 | 23 | 37 | 48 | 41 | 31 |
| 87 | 78 | 81 | 70 | 28 | 0 |
| 88 | 41 | 49 | 60 | 40 | 0 |
| 89 | 63 | 55 | 66 | 40 | 7 |
| 90 | 75 | 85 | 33 | 6 | 0 |
| 91 | 50 | 72 | 3 | 0 | 0 |
| 92 | 86 | 44 | 38 | 12 | 17 |
| 93 | 91 | 68 | 39 | 7 | 2 |
| 94 | 31 | 62 | 83 | 76 | 43 |
| 95 | 69 | 71 | 45 | 16 | 10 |
| 96 | 77 | 75 | 47 | 29 | 5 |
| 97 | 0 | 24 | 73 | 0 | 0 |
| 98 | 72 | 71 | 74 | 67 | 4 |

TABLE 3-continued

INHIBITION OF PAI-1 IN THE FIRST S2251 CHROMOGENIC SUBSTRATE ASSAY

| Compound No. | \multicolumn{5}{c}{Concentration in μm} |
|---|---|---|---|---|---|
| | 60 | 30 | 15 | 7.5 | 3.75 |
| 23 | 65 | 17 | 0 | 0 | |
| 24 | 56 | 29 | 0 | 0 | 0 |
| 26 | 57 | 71 | 73 | 42 | |
| 34 | 72 | 77 | 76 | 24 | |
| 42 | 58 | 57 | 59 | 4 | 1 |
| 64 | 100 | 87 | 63 | 17 | |
| 71 | 52 | 64 | 51 | 1 | 1 |
| 72 | 76 | 75 | 18 | 1 | 2 |

| Compound No. | \multicolumn{5}{c}{Concentration in μm} |
|---|---|---|---|---|---|
| | 40 | 20 | 10 | 5 | 2.5 |
| 99 | 68 | 48 | 17 | 0 | 0 |

| Compound No. | \multicolumn{5}{c}{Concentration in μm} |
|---|---|---|---|---|---|
| | 100 | 50 | 25 | 12 | 6 |
| 3 | 86 | 74 | 53 | 40 | 14 |

EXAMPLE 2

PHARMACEUTICAL COMPOSITION

Tablets, each weighing 0.15 g and containing 25 mg of a compound of the invention can be manufactured as follows:

Composition for 10,000 tablets

- compound of the invention (250 g)
- lactose (800 g)
- corn starch (415 g)
- talc powder (30 g)
- magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 3

PREPARATION OF (3Z,6Z)-3-BENZYLIDENE-6-(4-METHOXYBENZYLIDENE)-2,5-PIPERAZINEDIONE (3) (SCHEME1)

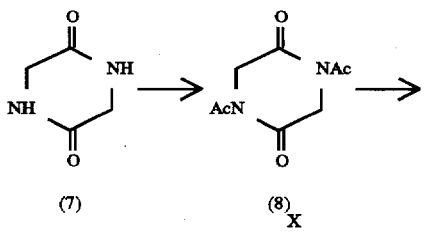

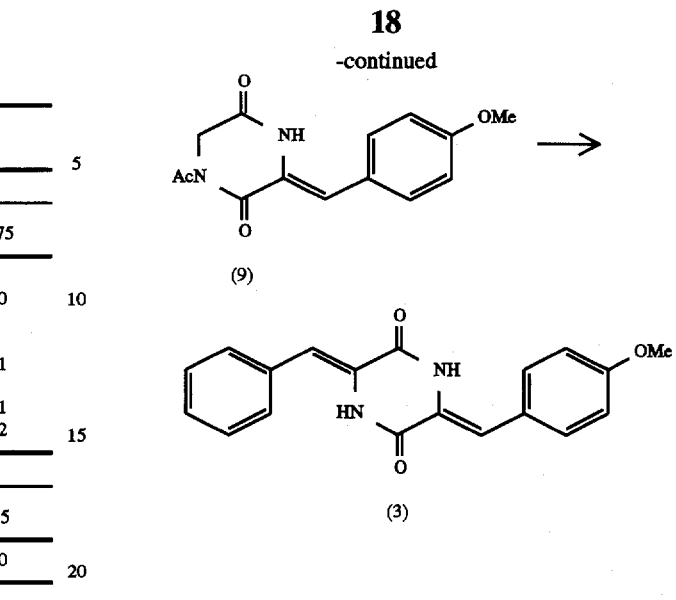

1,4-Diacetyl-2,5-piperazinedione (8)

1,4-Diacetyl-2,5-piperazine-2,5-dione (8) was prepared by the published procedure (S. M. Marcuccio and J. A. Elix, Aust. J. Chem., 1984, 37, 1791).

(3Z)-1-Acetyl-3-(4-methoxybenzylidene)-2,5-piperazinedione (9)

(3Z)-1-Acetyl-3-(4-methoxybenzylidene)-2,5-piperazinedione (9) was prepared by the published procedure (T. Yokoi, L.-M. Yang, T. Yokoi, R.-Y. Wu, and K.-H. Lee, J. Antibiot, 1988, 41, 494).

(3Z,6Z)-3-Benzylidene-6-(4-methoxybenzylidene)-2,5-piperazinedione (3)

A mixture of (3Z)-1-acetyl-3-(4-methoxybenzylidene)-2,5-piperazinedione (9) (1.0 g, 3.6 mmol), benzaldehyde (430 μl, 4.2 mmol) and triethylamine (1.14 ml), 8.2 mmol), in dry DMF (20 ml), was heated at 130° C. for 18 h. The reaction mixture was cooled to room temperature and poured into ethyl acetate (100 ml). A yellow solid precipitated which was filtered off and dried. Yield 360 mg (31%). $C_{19}H_{16}N_2O_3$ $^1$H nmr (400 MHz $d_6$-DMSO): δ: 3.80 (3H, s, o-Me); 6.77 (1H, s, CH=C); 6.78 (1H, s, CH=C); 6.98 (2H, d, J=8 Hz, 2×C—H on Ar—OMe); 7.30–7.56 (7H, m, Ph and 2×C—H on Ar—OMe); 10.15 (2H, br.s, N—H).

$^{13}$C nmr (100 MHz $d_6$-DMSO) δ: 58.68; 117.66; 118.03; 118.77; 128.11; 128.92; 129.95; 131.53; 132.11; 132.69; 134.44; 136.59; 161.39; 161.62; 162.71.

ms (desorption chemical ionisation, ammonia):

m/z (% relative intensity): 321 (100) MH$^+$.

ir: KBr (diffuse reflectance):

ν max (cm$^{-1}$): 1620, 1700, 3100, 3220.

Elemental analysis: Calculated for $C_{19}H_{16}N_2O_3$: C 71.24, H 5.03, N 8.74. Found: C 70.92, H 5.02, N 8.80. C 70.89, H 5.06, N 8.79

EXAMPLE 4

PREPARATION OF (3Z,6Z)-3-BENZYLIDENE-6-(4-METHOXYBENZYLIDENE)-1-METHYL-2,5-PIPERAZINEDIONE (1) (SCHEME 2)

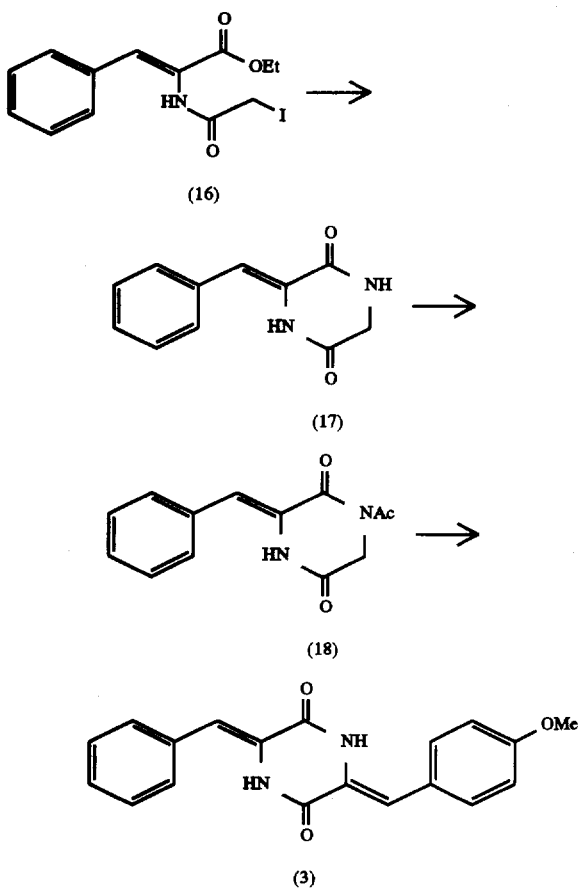

Compound 16 is treated with ammonia and subsequently with acetic anhydride to yield 1-acetyl-3-benzylidenepiperazine-2,5-dione (18).

Compound 18 is then condensed, in the presence of caesium carbonate or triethylamine in DMF, with 4-methoxybenzaldehyde to yield compound 3.

Reference Example 1

Preparation of 1-acetyl-3-benzylidene-2,5-piperazinedione 1,4-Diacetyl-2,5-piperazinedione (25.0 g, 126 mmol), which is compound (8) mentioned in Example 3, was heated at 120°–130° C. in DMF (200 ml) with triethylamine (17.6 ml, 126 mmol) and benzaldehyde (13.0 ml, 126 mmol). After 4 h the mixture was cooled to room temperature and poured into EtOAc (1000 ml), and washed three times with brine. Any solid formed at this stage was filtered off. The filtrate was dried (MgSO$_4$) and the solvent removed in vacuo. The residue was recrystallised from EtOAc:Hexane to give 11.78 g (38%) of the title compound as a yellow solid.

$^1$H NMR (CDCl$_3$ 400 MHz) δ=2.69 (3H, s) 4.54 (2H, s) 7.20 (1H, s) 7.40 (3H, m), 7.48 (2H, m), 7.93 (1H, br.s)

MS(DCI,NH$_3$): 262 (MNH$_4^+$, 20%), 245 (MH$^+$, 53%), 220 (52%), 204 (100%), 203 (100%)

| Microanalysis | C | H | N |
|---|---|---|---|
| Calc | 63.93 | 4.95 | 11.47 |
| Found | 64.11 | 5.02 | 11.41 |
|  | 64.05 | 4.90 | 11.44 |

EXAMPLE 5

Preparation of compound 96

1-Acetyl-3-benzylidene-2,5-piperazinedione (one equivalent), prepared according to Reference Example 1, was treated with 5-(4-formylphenoxy)pentanoic acid, methyl ester in the presence of Cs$_2$CO$_3$ (1–1.1 equivalents) in DMF at 80°–100° C. for 1–8 hours. The title compound was obtained in 39% yield.

By the same method, but replacing 5-(4-formylphenoxy)pentanoic acid, methyl ester (which is benzaldehyde substituted at position 4 by —O(CH$_2$)$_4$CO$_2$Me) by the appropriately substituted benzaldehyde, the following compounds were prepared:

| Compound | Yield (%) | Compound | Yield (%) |
|---|---|---|---|
| 21 | 66 | 25 | 37 |
| 34 | 56 | 43 | 54 |
| 38 | 84 | 45 | 91 |
| 44 | 44 | 51 | 68 |
| 48 | 69 | 54 | 69 |
| 52 | 72 | 59 | 50 |
| 55 | 73 | 62 | 63 |
| 61 | 44 | 75 | 49 |
| 66 | 15 | 85 | 15 |
| 76 | 60 | 89 | 37 |
| 90 | 74 | 93 | 69 |
| 94 | 39 | 95 | 26 |
| 96 | 39 | 102 | 45 |

Characterising data for the compounds are set out in Example 16.

EXAMPLE 6

Preparation of Compound 31

1-Acetyl-3-benzylidene-2,5-piperazinedione (one equivalent), prepared according to Reference Example 1, was treated with 3-acetoxybenzaldehyde (one equivalent) in the presence of triethylamine (1–2 equivalents) in DMF at 130° C. for 2–6 hours. The title compound was obtained in 61% yield.

By the same method, but replacing 3-acetoxybenzaldehyde by the appropriately substituted benzaldehyde, the following compounds were prepared:

| Compound | Yield (%) |
|---|---|
| 23 | 16 |
| 24 | 43 |
| 32 | 41 |
| 65 | 27 |
| 74 | 77 |
| 105 | 50 |

Characterising data are provided in Example 16.

EXAMPLE 7

Preparation of compound 103

1-Acetyl-3-(4-methoxybenzylidene)-2,5-piperazinedione (1 equivalent), which is compound (9) mentioned in Example 3, was treated with 2-fluorobenzaldehyde (1 equivalent) in the presence of $Cs_2CO_3$ (1–1.1 equivalents) in DMF at 80°–100° C. for 1–6 hours. The title compound was obtained in 69% yield.

By the same method, but replacing the 2-fluorobenzaldehyde by the appropriately substituted benzaldehyde with the exception of compound 84 which was prepared by condensation with 4-acetoxy-2-chlorobenzaldehyde, the following compounds were prepared:

| Compound | Yield (%) | Compound | Yield (%) |
|---|---|---|---|
| 26 | 80 | 63 | 71 |
| 29 | 70 | 69 | 20 |
| 37 | 21 | 70 | 10 |
| 41 | 34 | 73 | 38 |
| 46 | 16 | 80 | 45 |
| 47 | 46 | 81 | 5 |
| 49 | 60 | 83 | 41 |
| 50 | 56 | 84 | Low |
| 53 | 77 | 87 | 33 |
| 57 | 49 | 91 | 74 |
| 60 | 71 | 100 | 20 |
|  |  | 103 | 69 |

Characterising data are provided in Example 16.

EXAMPLE 8

Preparation of compound 28

1-Acetyl-3-(4-methoxybenzylidene)-2,5-piperazinedione (1 equivalent), compound (9) in Example 3, was treated with 2-nitrobenzaldehyde (1 equivalent) in triethylamine (1–2 equivalents) and DMF at 130° C. for 2–6 hours. The title compound was obtained in 45% yield. Characterising data are set out in Example 16.

Reference Example 2

Preparation of 1-acetyl-3-(4-acetamidobenzylidene)-2,5-piperazinedione 1,4-Diacetyl-2,5-piperazinedione (10.0 g, 50 mmol), prepared by the published procedure mentioned in Example 3, was stirred in DMF (40 ml) with 4-acetamidobenzaldehyde (8.24 g, 50 mmol) and triethylamine (7 ml, 50 mmol) and heated to 120° C. After 2½ h the mixture was cooled to room temperature, diluted with EtOAc (100 ml) and stirred overnight. The solid formed was collected, washed with EtOAc and dried to give 8.46 g (56%) of a yellow solid.

$^1$H NMR (CDCl$_3$+TFA, 400 MHz) δ=2.32 (3H, s) 2.72 (3H, s) 4.68 (2H, s) 7.36 (1H, s) 7.45 (2H, d, J=8 Hz) 7.60 (2H, d, J=8 Hz)

| Microanalysis | C | H | N |
|---|---|---|---|
| Calc | 59.80 | 5.02 | 13.95 |
| Found | 60.08 | 5.09 | 13.89 |
|  | 60.11 | 5.07 | 13.86 |

EXAMPLE 9

Preparation of Compound 77

1-Acetyl-3-(4-acetamidobenzylidene)-2,5-piperazinedione (1 equivalent), prepared according to Reference Example 2, was treated with 2,4-difluorobenzaldehyde (1 equivalent) in the presence of $Cs_2CO_3$ (1–1.1 equivalents) in DMF at 80°–100° C. for 1–6 hours. The title compound was obtained in 60% yield.

By the same method, but replacing 2,4-difluorobenzaldehyde by the appropriately substituted benzaldehyde, the following compounds were obtained:

| Compound | Yield (%) | Compound | Yield (%) |
|---|---|---|---|
| 42 | 50 | 40 | 40 |
| 68 | 26 | 58 | 22 |
| 72 | 41 | 71 | 36 |
| 79 | 11 | 78 | 16 |
| 92 | 68 | 82 | 16 |

Characterising data are set out in Example 16.

EXAMPLE 10

Preparation of compound 22

1,4-Diacetyl-2,5-piperazinedione (1 equivalent), prepared by the published procedure mentioned in Example 3, was treated with benzaldehyde (2.1 equivalents) in the presence of triethylamine (2.5 equivalents) in DMF at 130° C. for 8 hours. The title compound was obtained in 89% yield. Characterising data are set out in Example 16.

EXAMPLE 11

Preparation of compound 35

1,4-Diacetyl-2,5-piperazinedione (1 equivalent), prepared by the published procedure mentioned in Example 3, was treated with 3-nitrobenzaldehyde (1 equivalent) in the presence of triethylamine (1 equivalent) in DMF at room temperature for 18–20 hrs. The title compound was obtained in 9% yield together with 1-acetyl-3-(3-nitrobenzylidene)-2,5-piperazinedione (66% yield). Characterising data are set out in Example 16.

Reference Example 3

Preparation of 1-acetyl-3-(4-N,N-dimethylaminobenzylidine)-2,5-piperazinedione 1,4-Diacetyl-2,5-piperazinedione, (1 equivalent), prepared as described in Example 3, was treated with 4-N,N-dimethylaminobenzaldehyde (1 equivalent) in the presence of Et$_3$N in DMF at 130° C. for 24 hrs. The title compound was obtained in 18% yield

EXAMPLE 12

Preparation of Compound 86

1-Acetyl-3-(4-dimethylaminobenzylidene)-2,5-piperazinedione (1 equivalent) as described in Reference Example 3 was treated with 4-acetamidobenzaldehyde (1 equivalent) in the presence of $Cs_2CO_3$ (1 equivalent) in DMF at 80° C. for 2–6 hours. The title compound was obtained in 56% yield. Characterising data are set out in Example 16.

EXAMPLE 13

Interconversions of compounds of formula A (i) Compound 31, prepared as described in Example 6, was treated with aqueous lithium hydroxide in a mixture of MeOH and THF at room temperature for 2–3 hrs to give compound 33 in 91% yield.

(ii) Compound 61, prepared as described in Example 5, was treated with aqueous lithium hydroxide in a mixture of MeOH and THF at room temperature for 3 hours to give compound 64 in 57% yield.

(iii) Compound 96, prepared as described in Example 5, was treated with aqueous sodium hydroxide in THF at room temperature for 4 hours to give compound 97 in 54% yield.

(iv) Compound 37, prepared as described in Example 7, was treated with aqueous sodium hydroxide in THF at room temperature for 8 hrs to give compound 36 in 30% yield.

(v) Compound 56, prepared as described in Example 7, was treated with trifluoroacetic acid in $CH_2Cl_2$ at room temperature for 12 hrs to give compound 67 in 96% yield.

(vi) Compound 87, prepared as described in Example 7, was treated with aqueous sodium hydroxide in THF at room temperature for 4 hours to give compound 88 in 69% yield.

(vii) Compound 65, prepared as described in Example 6 was hydrogenated over 10% palladium on carbon as catalyst in $CH_2Cl_2$ in the presence of a few drops of trifluoroacetic acid to give compound 39 in 38% yield. Under the same conditions of hydrogenation compound 74 was converted into compound 30 in 95% yield.

(viii) Compound 93, prepared as described in Example 5, was hydrolysed by treatment with aqueous sodium hydroxide in a mixture of MeOH and THF at room temperature for 18 hours to give compound 101 in 72% yield.

(ix) Compound 58, prepared as described in Example 9, was hydrolysed by treatment with aqueous sodium hydroxide in THF at room temperature for 3 hours to give compound 104 in 90% yield.

Characterising data for all compounds prepared in this Example are provided in Example 16.

EXAMPLE 14

Preparation of Compound 27

1-Acetyl-3-(4-methoxybenzylidene)-2,5-piperazinedione (1 equivalent), compound (9) in Example 3, was treated with 2-naphthaldehyde (1 equivalent) in the presence of $Cs_2CO_3$ (1.0–1.1 equivalents) in DMF at 80°–100° C. for 1–6 hours. The title compound was obtained in 84% yield.

Characterising data are provided in Example 16.

EXAMPLE 15

Preparation of Salts

Compound 98, the hydrochloride salt of compound 102, was prepared by treatment of a solution of compound 102 in THF with 2 molar hydrochloric acid followed by sonication until a clear solution was obtained. The solvent was then removed in vacuo and the residual solution was freeze-dried to give compound 98.

Compound 99 was prepared by bubbling HCl gas through a solution of the corresponding free base in THF, followed by evaporation to dryness.

Characterising data are provided in Example 16.

EXAMPLE 16

Characterization of compounds of formula A

The compounds prepared in the preceding Examples, were characterised by mass spectroscopic, microanalytical, proton nuclear magnetic resonance and, in some cases, infra-red techniques. The results are set out in Table 2:

TABLE 2

| N° | Mol. Formula (M. Wt) | Mass spec m/z, mass, intensity (mode) | $^1H$ nmr Solvent δ all 400 MHz | | Microanalysis Calc | Found | Infra-red $cm^{-1}$ |
|---|---|---|---|---|---|---|---|
| 21 | $C_{18}H_{12}N_2O_2Cl_2$ | 359, MH+, 100%; 376, $MNH_4^+$, 15%; 363, 10%; 362, 10%; 361, 60%; 323, 40% (DCI, $NH_3$) | $d_6$-DMSO 7.6–7.30(m, 8H), 6.81(s, 1H), 6.60(s, 1H) | C H N Cl | 60.19 3.37 7.80 19.74 | 59.33 59.37 3.44 3.68 7.55 7.48 19.22 19.40 | 3200, 3050, 1680, 1620, 1400, 1370 |
| 22 | $C_{18}H_{14}O_2H_2$ (290) mixture of isomers | 291, MH+ (DCI, $NH_3$) | $d_6$-DMSO 6.54(1H, s), 6.71(1H, s), 6.80(2H, s), 7.20–7.60(20H, m), 10.17(2H, broad singlet), 10.80(0.5H, broad singlet) | C H N | 74.47 4.86 9.65 | 74.39 74.20 4.78 4.75 9.68 9.60 | |
| 23 | $C_{20}H_{16}N_2O_4$ | 348(M+, 23%); 306, 100% (EI) | $CDCl_3 + CF_3CO_2D$ 2.40(3H, s), 7.25 (2H, d, J=7Hz), 7.29(1H, s), 7.40–7.51(8H, m) | C H N | 68.96 4.63 8.04 | 69.05 69.08 4.56 4.57 8.15 8.15 | 1620, 1690, 1760, 3200 |
| 24 | $C_{18}H_{13}N_3O_4$ (335) | 336, MH+, 100%; 353, $MNH_4^+$, 10%; 306, 20%; 291, 70% (DCI/$NH_3$) | $CDCl_3 + CF_3CO_2D$ 8.30–8.26(m, 2H), 7.76–7.67(m, 2H), 7.53–7.43(m, 5H), 7.32(s, 1H), 7.26(s, 1H) | C H N | 64.48 3.91 12.53 | 65.06 65.03 3.93 3.98 12.19 12.20 | |

TABLE 2-continued

| N° | Mol. Formula (M. Wt) | Mass spec m/z, mass, intensity (mode) | $^1$H nmr Solvent δ all 400 MHz | Microanalysis | Calc | Found | Infra-red cm$^{-1}$ |
|---|---|---|---|---|---|---|---|
| 25 | $C_{20}H_{18}N_2O_3$ (334) | 335, MH$^+$, 100%; 305, 10%; 291, 20%; 277, 10%; 161, 20% (DCI/NH$_3$) | CDCl$_3$ + CF$_3$CO$_2$D 7.49–7.39(m, 7H), 7.20(d, 2H), 7.00(d, 2H), 4.11(q, 2H), 1.45(t, 3H) | C H N | 71.84 5.43 8.38 | 71.83 5.35 8.38 | 71.95 5.36 8.41 |
| 26 | $C_{21}H_{19}N_3O_4$ (377) | 279, 10%; 378 MH$^+$; 395, MNH$_4^+$, 50% (DCI/NH$_3$) | CDCl$_3$ + CF$_3$CO$_2$D 7.60(1.62H, d), 7.55(0.38H, d), 7.50(3.55H, m), 7.45(0.45H, d), 7.28(1H, s), 7.22(1H, s), 7.05(2H, d), 3.90(3H, s), 2.38(2.5H, s), 2.25(0.5H, s) | C H N | 66.83 5.07 11.13 | 66.77 5.04 11.07 | 66.94 4.96 11.10 |
| 27 | $C_{23}H_{18}N_2O_2$ | 371, MH$^+$; 388, MNH$_4^+$, 2% (DCI/NH$_3$) | CDCl$_3$ + CF$_3$CO$_2$D 8.02(1H, s), 7.95(2H, m), 7.90(1H, m), 7.58(2H, m), 7.50(1H, dd), 7.48(2H, d), 7.40(1H, s), 7.25(1H, s), 7.05(2H, d), 3.90(3H, s) | C H N | 74.58 4.90 7.56 | 74.48 4.86 7.55 | 74.39 4.93 7.58 |
| 28 | $C_{19}H_{15}N_3O_5$ (365) | 366, MH$^+$; 383, MNH$_4^+$, 80% (DCI/NH$_3$) | CDCl$_3$+CF$_3$CO$_2$D 8.30(1H, d), 7.77(1H, m), 7.67(1H, m), 7.48(4H, m), 7.25(1H, s), 7.02(2H, d), 3.90(3H, s) | C H N | 62.46 4.13 11.50 | 62.55 4.17 11.60 | 62.45 4.16 11.50 |
| 29 | $C_{19}H_{14}N_2O_3Cl_2$ | 355, 15%; 389, MH$^+$; 406, MNH$_4^+$, 2% (DCI/NH$_3$) | CDCl$_3$+CF$_3$CO$_2$D 7.40(4H, m), 7.35(1H, pt), 7.25(1H, s), 7.10(1H, s), 7.02(2H, d), 3.90(3H, s) | C H N | 58.63 3.63 7.20 | 58.40 3.64 7.13 | 58.41 3.66 7.12 |
| 30 | $C_{18}H_{15}N_3O_2$ (305) | 306, MH$^+$, 100% (DCI/NH$_3$) | CDCl$_3$ + CF$_3$CO$_2$D 7.59(d, 2H), 7.53(d, 2H), 7.51–7.42(m, 5H), 7.31(s, 1H), 7.22(s, 1H) | | | | |
| 31 | $C_{20}H_{16}N_2O_4$ (348) | 349, MH$^+$, 100%; 366, MNH$_4^+$, 10% (DCI/NH$_3$) | CDCl$_3$ + CF$_3$CO$_2$D 2.39(3H, s), 7.14–7.54(11H, m) | C H N | 68.96 4.63 8.04 | 69.14 4.63 8.07 | 69.16 4.63 8.00 |
| 32 | $C_{20}H_{16}N_2O_4$ (348) | 366, MNH$_4^+$, 38%; 349, MH$^+$, 100% (DCI/NH$_3$) | CDCl$_3$ 2.40(3H, s), 6.90(1H, s), 7.04(1H, s), 7.20(1H, d), 7.30–7.50(8H, m), 8.12(1H, bs), 8.19(1H, bs) | C H N | 68.96 4.63 8.04 | 68.88 4.56 8.30 | 69.07 4.55 8.30 |
| 33 | $C_{18}H_{14}N_2O_3$ (306) | 324, MNH$_4^+$, 5%; 307, MH$^+$, 100% (DCI/NH$_3$) | CDCl$_3$ + CF$_3$CO$_2$D 6.97–7.50(11H, m) | | | | |
| 34 | $C_{20}H_{17}N_3O_3$ (347) | 348, MH$^+$, 100%; 305, 70%; 227, 30%; 145, 80% (DCI$^+$) (DCI/NH$_3$) | CDCl$_3$ + CF$_3$CO$_2$D 7.61(d, 2H), 7.55–7.43(m, 7H), 7.29(s, 1H), 7.24(s, 1H), 2.37+2.25 (singlets, 3H,) (2.37–77%, 2.25–23%) | C H N | 69.15 4.93 12.10 | 68.87 4.73 11.93 | 68.96 4.86 11.91 |
| 35 | $C_{18}H_{12}O_6N_4$ | 380, MH$^+$, 30%; | CDCl$_3$, CF$_3$CO$_2$D | C | 56.85 | 56.84 | 56.74 |

TABLE 2-continued

| N° | Mol. Formula (M. Wt) | Mass spec m/z, mass, intensity (mode) | ¹H nmr Solvent δ all 400 MHz | | Microanalysis Calc | Found | | Infra-red cm⁻¹ |
|---|---|---|---|---|---|---|---|---|
| | (380) | 398, MNH₄⁺, 100% (DCI/NH₃) | 8.37–8.34(m, 4H), 7.83–7.70(m, 4H), 7.40(s, 2H) | H N | 3.18 14.73 | 3.04 14.69 | 3.05 14.67 | |
| 36 | C₁₉H₁₆N₂O₄ (336) | 337, MH⁺; 351, MNH₄⁺, 5% (DCI/NH₃) | CDCl₃ + CF₃CO₂D 7.40(4H, m), 7.22(2H, d), 7.00(2H, d), 6.98(2H, d), 3.90(3H, s) | | | | | |
| 37 | C₂₁H₁₈N₂O₅ (378) | 379, MH⁺; 396, MNH₄⁺, 40% (DCI/NH₃) | CDCl₃ + CF₃CO₂D 7.48(2H, d), 7.44(2H, d), 7.20(4H, m), 7.02(2H, d), 3.90(3H, s), 2.40(3H, s) | C H N | 66.66 4.79 7.40 | 66.38 4.71 7.35 | 66.63 4.71 7.41 | |
| 38 | C₂₀H₁₇N₃O₃ (347) | 348, MH⁺, 100%; 365, MNH₄⁺, 10%; 331, 10%; 306, 10% (DCI/NH₃) | CDCl₃ + CF₃CO₂D 7.70–7.68(m, 1H), 7.52–7.38(m, 8H), 7.28(s, 1H), 7.14(s, 1H), 2.30+2.08 (singlets, 3H) | C H N | 69.15 4.93 12.10 | 68.21 4.86 11.79 | 68.47 4.89 11.85 | |
| 39 | C₁₈H₁₅N₃O₂ (305) | 306, MH⁺, 100% (DCI/NH₃) | CDCl₃ + CF₃CO₂D 7.62–7.48(m, 9H), 7.28(s, 1H), 7.17(s, 1H) | | | | | |
| 40 | C₂₀H₁₅N₃O₃Cl₂ (415) | 433/435, MNH₄⁺, 100%; 416/418, MH⁺, 55%; 380, 13% (DCI/NH₃) | CDCl₃ + CF₃CO₂D 2.36(3H, s), 7.14(1H, s), 7.26(1H, s), 7.34(1H, m), 7.42(2H, d), 7.49(2H, d), 7.60(2H, d) | C H N | 57.71 3.63 10.09 | 57.51 3.81 10.34 | 57.55 3.88 10.13 | |
| 41 | C₂₂H₂₁N₃O₄ (391) | 409, MNH₄⁺, 29%; 392, MH⁺, 100%; 350, 32% (DCI/NH₃) | CDCl₃ + CF₃CO₂D 2.02(3H, s), 3.34(3H, s), 3.89(3H, s), 7.01(2H, d), 7.21(1H, s), 7.22(1H, s), 7.33(2H, d), 7.43(2H, d), 7.52(2H, d) | C H N | 67.50 5.41 10.74 | 66.75 5.34 10.57 | 66.63 5.36 10.52 | |
| 42 | C₂₀H₁₆N₃O₃Cl (381) | 399, MNH₄⁺, 70%; 401, 32%; 382, MH⁺, 100%; 384, 55% (DCI/NH₃) | CDCl₃ + CF₃CO₂D 2.35(3H, s), 7.21(2H, d), 7.49(2H, d), 7.50(4H, m), 7.61(2H, d) | | | | | |
| 43 | C₂₁H₁₈N₂O₄ (362) | 380, MNH₄⁺, 70%; 363, MH⁺, 100%; 303, 44%; 291, 13%; 279, 11% (DCI/NH₃) | CDCl₃ + CF₃CO₂D 2.19(3H, s), 5.2(2H, s), 7.25(2H, d), 7.40–7.52(9H, m) | C H N | 69.60 5.01 7.73 | 69.72 4.95 7.79 | 69.86 4.94 7.79 | |
| 44 | C₂₁H₁₉N₃O₃ (361) | 379, MNH₄⁺, 10%; 362, MH⁺, 100%; 319, 10%; 291, 11% (DCI/NH₃) | CDCl₃ + CF₃CO₂D 2.19(3H, s), 5.30, 4.51(2H, s), 7.21(2H, s), 7.32–7.52(9H, m) | C H N | 69.79 5.30 11.63 | 69.32 5.38 11.29 | 69.19 5.26 11.13 | |
| 45 | C₁₈H₁₄N₂O₂ (290) | | d₆-DMSO 6.78(2H, s), 7.35(2H, t), 7.40(4H, t), 7.56(4H, d) | C H N | 74.47 4.86 9.65 | 73.95 4.80 9.57 | 73.92 4.81 9.56 | |
| 46 | C₂₀H₁₈N₂O₅S (398) | 351, 30%; 399, MH⁺; 416, MNH₄⁺ (DCI/NH₃) | CDCl₃ 8.07(2H, d), 7.65(2H, d), 7.47(2H, d), 7.25(2H), 7.05(2H, d), | C H N | 60.29 4.55 7.03 | 59.89 4.54 6.90 | 59.99 4.56 6.96 | |

TABLE 2-continued

| N° | Mol. Formula (M. Wt) | Mass spec m/z, mass, intensity (mode) | ¹H nmr Solvent δ all 400 MHz | Microanalysis | Calc | Found | Infra-red cm⁻¹ |
|---|---|---|---|---|---|---|---|
| | | | 3.90(3H, s), 3.18(3H, s) | | | | |
| 47 | $C_{23}H_{24}N_2O_4$ (392) | MH⁺ 393 (DCI/NH₃) | CDCl₃+CF₃CO₂D 7.40(4H, m), 7.20(2H, s), 7.00(4H, m), 4.08(2H, t), 3.88(3H, s), 1.82(2H, m), 1.53(2H, m), 1.00(3H, t) | C H N | 70.39 6.16 7.14 | 70.06 70.13 6.06 6.10 7.20 7.13 | |
| 48 | $C_{22}H_{22}N_2O_3$ (362) | MH⁺ 363 (DCI/NH₃) | CDCl₃+CF₃CO₂D 7.48(7H, m), 7.25(2H, d), 7.00(2H, d), 4.05(2H, t), 1.82(2H, m), 1.48(2H, m), 0.98(3H, t) | C H N | 72.91 6.12 7.73 | 72.14 72.09 5.79 5.99 7.71 7.69 | |
| 49 | $C_{22}H_{22}N_2O_4$ (378) | MH⁺ 379 (DCI/NH₃) | CDCl₃+CF₃CO₂D 7.38(4H, m), 7.18(2H, s), 6.98(4H, pt), 4.62(1H, m), 3.88(3H, s), 1.38(6H, d) | C H N | 69.83 5.86 7.40 | 69.85 69.90 5.76 5.80 7.41 7.42 | |
| 50 | $C_{23}H_{24}N_2O_3$ (376) | MH⁺ 377 (DCI/NH₃) | CDCl₃+CF₃CO₂D 7.55(2H, d), 7.45(2H, d), 7.40(2H, d), 7.25(2H), 7.05(2H, d), 3.90(3H, s), 1.35(9H, s) | C H N | 73.38 6.43 7.44 | 73.21 73.29 6.45 6.45 7.44 7.44 | |
| 51 | $C_{22}H_{22}N_2O_2$ | 331, MH⁺, 10%; 347, MNH₄⁺, 364 (DCI/NH₃) | CDCl₃ + CF₃CO₂D 7.48(7H, m), 7.39(2H, d), 7.25(2H), 1.35(9H, s) | C H N | 76.28 6.40 8.09 | 75.57 75.53 6.28 6.34 8.04 8.04 | |
| 52 | $C_{21}H_{20}N_2O_3$ | 291, 10%; 349, MH⁺ (DCI/NH₃) | CDCl₃+CF₃CO₂D 7.45(7H, m), 7.25(1H, s), 7.23(1H, s), 7.02(2H, d), 4.55(1H, m), 1.40(6H, d) | C H N | 72.40 5.79 8.04 | 72.30 72.42 5.76 5.65 8.15 8.12 | |
| 53 | $C_{19}H_{15}N_2O_3Br$ (399 ± 1) | 399:401 (100:100)%; 321 62% (DCI/NH₃) | CDCl₃ + CF₃CO₂D 3.88(3H, s), 7.01(2H, d), 7.19(1H, s), 7.22(1H, s), 7.28–7.31(1H, m), 7.36–7.43(4H, m), 7.70(1H, d) | C H N Br | 57.16 3.79 7.02 20.01 | 57.08 56.95 3.77 3.78 6.94 6.96 20.03 | |
| 54 | $C_{18}H_{12}N_2O_2F_2$ (326) | 327, 100% (DCI/NH₃) | CDCl₃ + CF₃CO₂D 6.90–7.03(2H, m), 7.15(1H, s), 7.31(1H, s), 7.38–7.52(6H, m) | C H N | 66.26 3.71 8.59 | 66.44 66.50 3.74 3.72 8.65 8.66 | |
| 55 | $C_{18}H_{13}N_2O_2Br$ (369 ± 1) | 369:371, (100:100)%; 386:388, (19:19)%; 291, 63% (DCI/NH₃) | CDCl₃ + CF₃CO₂D 7.29–7.33(2H, m), 7.39–7.53(8H, m), 7.71(1H, d) | C H N Br | 58.56 3.55 7.59 21.64 | 58.57 58.28 3.45 3.46 7.62 7.47 21.33 21.35 | |
| 56 | $C_{25}H_{27}N_3O_5$ (449) | 467, MNH₄⁺, 3%; 450, MH⁺, 7%; 449, M⁺, 12%; 394, 100%; 351, 14%; 333, 16% (DCI/NH₃) | CDCl₃ + CF₃CO₂D 1.48(9H, s), 3.90(3H, s), 4.34(2H, s), 7.03(2H, d), 7.21(1H, s), 7.33–7.47(6H, m), 7.51(1H, s) | C H N | 66.80 6.05 9.35 | 66.45 66.50 5.97 5.94 9.28 9.29 | |

TABLE 2-continued

| N° | Mol. Formula (M. Wt) | Mass spec m/z, mass, intensity (mode) | ¹H nmr Solvent δ all 400 MHz | Microanalysis | Calc | Found | Infra-red $cm^{-1}$ |
|---|---|---|---|---|---|---|---|
| 57 | $C_{21}H_{20}N_2O_3S$ (380) | 398, $MNH_4^+$, 4%; 381, $MH^+$, 100%; 333, 24% ($DCI/NH_3$) | $CDCl_3 + CF_3CO_2D$ 2.02(3H, s), 3.71(2H, s), 3.39(3H, s), 7.02(2H, d), 7.21(2H, s), 7.38–7.49(6H, m) | C H N S | 66.30 5.30 7.36 8.43 | 65.87 5.16 7.32 7.45 | 65.82 5.14 7.30 7.62 |
| 58 | $C_{23}H_{21}N_3O_5$ (419) | 437, $MNH_4^+$, 18%; 420, $MH^+$, 90%; 405, 30%; 360, 100%; 317, 8% ($DCI/NH_3$) | $CDCl_3 + CF_3CO_2D$ 2.21(3H, s), 2.34(3H, s), 5.21(2H, s), 7.25(2H, d), 7.41–7.50(6H, m), 7.59(2H, d) | | | | |
| 59 | $C_{20}H_{18}N_2O_{2S}$ (350) | 368, $MNH_4^+$, 8%; 351, $MH^+$, 100%; 303, 31%; 291, 8% ($DCI/NH_3$) | $CDCl_3 + CF_3CO_2D$ 2.03(3H, s), 3.72(2H, s), 7.28(1H, s), 7.38–7.51(10H, m) | C H N | 68.55 5.18 7.99 | 67.94 5.00 8.01 | 67.89 4.99 8.00 |
| 60 | $C_{21}H_{20}N_2O_5S$ (412) | 430, $MNH_4^+$, 28%; 413, $MH^+$, 100%; 333, 35% ($DCI/NH_3$) | $CDCl_3 + CF_3CO_2D$ 2.96(3H, s), 3.91(3H, s), 4.45(2H, s), 7.08(2H, d), 7.24(2H, d), 7.42(2H, d), 7.51(4H, m) | C H N S | 61.15 4.89 6.79 7.77 | 60.86 4.83 6.83 7.37 | 60.83 4.83 6.83 7.47 |
| 61 | $C_{21}H_{18}N_2O_3S$ (378) | 379, $MH^+$, 100%; 337, 8%; 305, 8% ($DCI/NH_3$) | $CDCl_3 + CF_3CO_2D$ 2.39(3H, s), 4.15(2H, s), 7.15–7.50(11H, m) | C H N | 66.65 4.79 7.40 | 66.28 4.71 7.58 | 66.20 4.74 7.61 |
| 62 | $C_{20}H_{16}N_2O_4$ (348) | 366, $M^+NH_4$, 40%; 349, $M^+H$, 100% ($DCI/NH_3$) | $CDCl_3 + CF_3CO_2D$ 4.00(3H, s), 7.25–7.69(9H, m), 8.09–8.14(2H, m) | | | | |
| 63 | $C_{22}H_{20}N_2O_4S$ (408) | 409, $M^+H$, 100% ($DCI/NH_3$) | $CDCl_3 + CF_3CO_2D$ 2.40(3H, s), 3.87(3H, s), 4.18(2H, s), 7.00(2H, d), 7.16–7.43(8H, m) | | | | |
| 64 | $C_{19}H_{16}N_2O_2S$ (336) | 354, $M^+NH_4$, 12%; 337, $M^+H$, 100%; 305, 30% ($DCI/NH_3$) | $CDCl_3 + CF_3CO_2D$ 3.65(2H, s), 7.20–7.55(11H, m) | | | | |
| 65 | $C_{19}H_{13}N_3O_4$ (335) | 336, $MH^+$, 100%; 353, $MNH_4^+$, 20%; 306, 30%; 291, 30% ($DCI/NH_3$) | $CDCl_3, CF_3CO_2D$ 8.31(1H, d), 7.78(1H, m), 7.65(1H, m), 7.55–7.52(7H m), 7.31(1H, s) | C H N | 67.45 4.47 8.28 | 67.44 4.37 8.27 | 67.44 4.32 8.29 |
| 66 | $C_{24}H_{25}N_3O_4$ (419) | 437, $MNH_4^+$, 5%; 420, $MH^+$, 6%; 381, 17%; 364, 100%; 318, 13%; 303, 9%; 291, 32% ($DCI/NH_3$) | $d_6$-DMSO 1.40(9H, s), 4.12(2H, d), 6.77(2H, d), 7.22–7.56(9H, m) | C H N | 68.72 6.01 10.02 | 68.83 5.89 9.81 | 68.80 5.85 9.83 |
| 67 | $C_{20}H_{19}N_3O_3$ (349) | 350, $MH^+$, 12%; 349, $M^+$, 13%; 333, 100% ($DCI/NH_3$) | $CDCl_3 + CF_3CO_2D$ 3.92(3H, s), 4.32(2H, s), 7.05(2H, d), 7.24(2H), 7.45(2H, d), 7.52(4H, s) | | | | |
| 68 | $C_{26}H_{28}N_4O_5$ (476) | 494, $MNH_4^+$, 10%; 477, $MH^+$, 18%; 476, $M^+$, 17%; 438, 22%; 421, 100%; 405, 9%; 375, 6%; 360, 28% ($DCI/NH_3$) | $d_6$-DMSO 2.09(3H, s), 2.10(9H, s), 4.12(2H, d), 6.71(2H, d), 7.26(2H), 7.49(4H, m), 7.61(2H, d) | | | | |

TABLE 2-continued

| N° | Mol. Formula (M. Wt) | Mass spec m/z, mass, intensity (mode) | $^1$H nmr Solvent δ all 400 MHz | Microanalysis | Calc | Found | Infra-red cm$^{-1}$ |
|---|---|---|---|---|---|---|---|
| 69 | $C_{19}H_{14}N_2O_3F_2$ (356) | 357, 100% (DCI/NH$_3$) | CDCl$_3$ + CF$_3$CO$_2$D 3.88(3H, s), 6.90–7.20(4H, m), 7.11(1H, s), 7.22(1H, s), 7.37–7.44(3H, m) | C H N | 64.04 3.96 7.86 | 63.47 3.86 7.79 | 63.36 3.82 7.77 |
| 70 | $C_{20}H_{15}N_2O_3F_3$ (388) | 389, 100; 406, 19% (DCI/NH$_3$) | CDCl$_3$ + CF$_3$CO$_2$D 3.90(3H, s), 7.04(2H, d), 7.23(1H, s), 7.37–7.47(4H, m), 7.55(1H, t), 7.62(1H, t), 7.80(1H, d) | | | | |
| 71 | $C_{20}H_{16}N_3O_3F$ | | CDCl$_3$ + CF$_3$CO$_2$D 2.36(3H, s), 7.18–7.30(4H, m), 7.40–7.50(4H, m), 7.58(2H, d) | | | | |
| 72 | $C_{20}H_{16}N_3O_3F$ (365) | 383, 21%; 366, 100%; 323, 12% (DCI/NH$_3$) | CDCl$_3$ + CF$_3$CO$_2$D 2.36(3H, s), 7.17–7.28(4H, m), 7.41–7.49(4H, m) 7.60(2H, d) | | | | |
| 73 | $C_{21}H_{20}N_2O_5$ | | CDCl$_3$ + CF$_3$CO$_2$D 3.90(6H, s), 3.99(3H, s), 6.60(1H, s), 7.01(2H, d, J=6Hz), 7.19(2H, m), 7.30(1H, s), 7.32(1H, s), 7.40(2H, d, J=6Hz) | C H N | 66.31 5.30 7.36 | 66.12 5.25 7.35 | 66.13 5.22 7.33 |
| 74 | $C_{18}H_{13}N_3O_4$ (335) | 336, MH$^+$, 100%; 353, MNH$_4^+$, 20%; 306, 30%; 291, 30% (DCI/NH$_3$) | CDCl$_3$ + CF$_3$CO$_2$D 8.35(d, 2H), 7.62(d, 2H), 7.55–7.42(m, 5H), 7.36(s, 1H), 7.28(s, 1H) | C H N | 64.48 3.91 12.53 | 64.55 3.90 12.41 | 64.57 3.89 12.41 | 3250, 1690, 1620, 1570, 1420, 1370 |
| 75 | $C_{23}H_{25}N_3O_3$ | 392, MH$^+$, 100% (DCI/NH$_3$) | CDCl$_3$ + CF$_3$CO$_2$D 2.30(2H, m), 3.01(6H, s), 3.43(2H, m), 4.15(2H, m), 6.96(2H, d, J=8Hz), 7.23(1H, s), 7.40–7.55(8H, m) | C H N | 70.57 6.44 10.73 | 70.28 6.33 10.59 | 70.46 6.36 10.68 |
| 76 | $C_{21}H_{16}N_2O_3S$ | 396, MNH$_4^+$, 4%; 379, MH$^+$, 100% (DCI/NH$_3$) | CDCl$_3$ + CF$_3$CO$_2$D 7.53–7.34(10H, m), 7.21(1H, s), 4.18(2H, s), 2.42(3H, s) | C H N | 66.65 4.79 7.40 | 66.79 4.69 7.41 | 66.82 4.71 7.41 |
| 77 | $C_{20}H_{15}N_3O_3S_2$ (383) | 401, 100%; 384, 75% (DCI/NH$_3$) | CDCl$_3$ + CF$_3$CO$_2$D 2.37(3H, s), 6.90–7.05(2H, m), 7.18(1H, s), 7.27(1H, s), 7.39–7.50(3H, m), 7.60(2H, d) | C H N | 62.66 3.94 10.96 | 62.65 4.11 11.32 | 62.63 4.11 11.33 |
| 78 | $C_{21}H_{16}N_3O_3F_3$ (415) | 416, 100%; 433, 100% (DCI/NH$_3$) | CDCl$_3$ + CF$_3$CO$_2$D 2.37(3H, s), 7.22(1H, s), 7.42–7.49(4H, m), 7.56–7.70(4H, m), 7.32(1H, d) | C H N | 60.72 3.88 10.12 | 60.08 4.14 10.84 | 60.11 4.15 10.87 |
| 79 | $C_{20}H_{16}N_3O_3Br$ (426 ± 1) | 426:428, (41:41)%; 443:445, (100:100)% | CDCl$_3$ + CF$_3$CO$_2$D 2.36(3H, s), 7.22(1H, s), 7.29–7.35(2H, m), | C H N | 56.35 3.78 9.86 | 56.65 3.92 9.97 | 56.79 3.84 10.01 |

TABLE 2-continued

| N° | Mol. Formula (M. Wt) | Mass spec m/z, mass, intensity (mode) | $^1$H nmr Solvent δ all 400 MHz | Microanalysis | | | Infra-red cm$^{-1}$ |
|---|---|---|---|---|---|---|---|
| | | | | | Calc | Found | |
| | | (DCI/NH$_3$) | 7.38–7.49(4H, m), 7.60(2H, d), 7.72(1H, d) | | | | |
| 80 | C$_{20}$H$_{17}$N$_3$O$_4$ (363) | 351, 10%, MH$^+$, 364 (DCI/NH$_3$) | d$_6$-DMSO 7.98(1H, bs), 7.90(2H, d), 7.60(2H, d), 7.55(2H, d), 7.40(1H, bs), 7.00(2H, d), 6.78(2H, m), 3.79(3H, s) | C H N | 66.11 4.72 11.56 | 65.57 65.49 4.71 4.71 11.32 11.31 | |
| 81 | C$_{24}$H$_{24}$N$_2$O$_5$ (420) | 336, 20%; 351, 15%; 379, 25%; 421, MH$^+$, 100%, MNH$_4^+$, 438, 10% (DCI/NH$_3$) | CDCl$_3$+CF$_3$CO$_2$D 7.48(2H, d), 7.45(2H, d), 7.20(4H, m), 7.02(2H, d), 3.90(3H, s), 1.38(9H, s) | | | | |
| 82 | C$_{29}$H$_{29}$N$_3$O$_5$ (447) | 363, 25%; 406, 15%; 448, MH$^+$ 100% (DCI/NH$_3$) | CDCl$_3$+CF$_3$CO$_2$D 7.62(2H, d), 7.48(4H, m), 7.25(2H, d), 7.20(2H, d), 2.35(3H, s), 1.40(9H, s) | | | | |
| 83 | C$_{21}$H$_{19}$N$_3$O$_5$ | 411, MNH$_4^+$, 10%; 394, MH$^+$, 100%; 362, 57% (DCI/NH$_3$) | d$_6$-DMSO 3.68(3H, s), 3.80(3H, s), 6.57(1H, s), 6.60(1H, s), 6.95(2H, d, J=7Hz), 7.47(2H, d, J=7Hz), 7.67(4H, m), 9.68(1H, br.s), 9.78(2H, br.s) | | | | |
| 84 | C$_{19}$H$_{15}$N$_2$O$_4$Cl (370/372) | 371, MH$^+$, 100%; 373, 30%; 388, MNH$_4^+$, 45% (DCI/NH$_3$) | d$_6$-DMSO 10.08(s, 2H), 7.52(d, 2H), 7.45(d, 1H), 6.98(d, 2H), 6.90(d, 1H), 6.80(dd, 1H), 6.76(s, 1H), 6.74(s, 1H), 3.79(s, 3H) | | | | |
| 85 | C$_{18}$H$_{13}$N$_2$O$_3$Cl (340/342) | 341, MH$^+$, 100%; 343, 30%; 358, MNH$_4^+$, 5%; 305, 50% (DCI/NH$_3$) | d$_6$-DMSO 8.98(s, 1H), 8.91(s, 1H), 8.88(s, 1H), 7.58(d, 2H), 7.50(d, 1H), 7.45(m, 2H), 7.37(m, 1H), 6.94(d, 1H), 6.83(dd, 1H), 6.80(s, 1H), 6.79(s, 1H) | | | | |
| 86 | C$_{22}$H$_{22}$N$_4$O$_3$ (390) | 391, MH$^+$, 100%; 408, MNH$_4^+$, 5% (DCI/NH$_3$) | CDCl$_3$ + CF$_3$CO$_2$D 7.66–7.58(m, 6H), 7.46(2H), 7.24(2H), 3.35(s, 6H), 2.35(s, 3H) | C H N | 67.68 5.68 14.35 | 66.97 66.70 5.64 5.50 14.35 14.15 | |
| 87 | C$_{23}$H$_{21}$N$_3$O$_6$ | 453, MNH$_4^+$, 30%; 436, MH$^+$, 100% (DCI/NH$_3$) | CDCl$_3$ + CF$_3$CO$_2$D 2.32(3H, s), 3.92(3H, s), 4.89(2H, s), 7.03(2H, d, J=6Hz), 7.24(1H, s), | | | | |

TABLE 2-continued

| N° | Mol. Formula (M. Wt) | Mass spec m/z, mass, intensity (mode) | ¹H nmr Solvent δ all 400 MHz | Microanalysis | Calc | Found | Infra-red cm⁻¹ |
|---|---|---|---|---|---|---|---|
| | | | 7.28(1H, s), 7.46(2H, d, J=6Hz), 7.50(2H, d, J=7Hz), 7.64(2H, d, J=7Hz) | | | | |
| 88 | $C_{21}H_{19}N_3O_5$ | 411, MNH₄⁺, 51%; 394, MH⁺, 100%; 336, 52% (DCI/NH₃) | CDCl₃ + CF₃CO₂D 3.92(3H, s), 4.57(2H, br.s), 7.08(2H, d, J=7Hz), 7.25(1H, s), 7.28(1H, s), 7.49(2H, d, J=7Hz), 7.50(2H, d, J=7Hz), 7.70(2H, d, J=7Hz) | | | | |
| 89 | $C_{24}H_{21}N_3O_2$ (383) | 384, MH⁺, 100%; 356, 5%; 296, 5% (DCI/NH₃) | CDCl₃ + CF₃CO₂D 8.26(d, 1H), 8.07(d, 1H), 7.86(m, 1H), 7.78(d, 1H), 7.74(d, 1H), 7.68(m, 2H), 7.55–7.45(m, 5H), 7.29(s, 1H), 3.55(s, 6H) | C H N | 75.18 5.52 10.96 | 74.92 5.50 10.99 | 74.81 5.52 11.02 |
| 90 | $C_{20}H_{18}N_2O_4$ (350) | 351, M⁺+1, 100% (EI) | CDCl₃ + CF₃CO₂D 3.90(3H, s, OMe), 3.95(3H, s, OMe), 6.90–7.50(10H, m) | | | | |
| 91 | $C_{21}H_{20}N_2O_5$ (380) | 381, 100% (EI) | CDCl₃ + CF₃CO₂D 3.85(3H, s, OMe), 3.90(3H, s, OMe), 3.95(3H, s, OMe), 6.90–7.45(9H, m) | C H N | 66.31 5.30 7.36 | 66.40 5.27 7.34 | 66.20 5.16 7.36 |
| 92 | $C_{22}H_{21}N_3O_5$ (407) | 425, M⁺NH₄, 25%; 408, MH⁺, 100% (DCI/NH₃) | CDCl₃ + CF₃CO₂D 2.35(3H, s, Ac), 3.90(3H, s, OMe), 3.95(3H, s, OMe), 6.90–7.60(9H, m) | C H N | 64.86 5.20 10.31 | 64.27 5.15 10.54 | 64.13 5.15 10.53 |
| 93 | $C_{21}H_{18}N_2O_5$ (378) | 396, M⁺NH₄, 15%; 379, MH⁺, 100% (DCI/NH₃) | CDCl₃ + CF₃CO₂D 3.90(3H, s, Me), 4.75(2H, s, CH₂), 6.95–7.50(11H, m) | C H N | 66.66 4.79 7.40 | 66.77 4.80 7.76 | 66.83 4.82 7.79 |
| 94 | $C_{25}H_{25}H_3O_5$ (447) | 465, M⁺NH₄, 15%; 448, MH⁺, 100%; 416, M⁺—OMe, 20% (DCI/NH₃) | CDCl₃ + CF₃CO₂D 2.00–2.05(2H, m), 2.43–2.50(4H, m), 3.75(3H, s, Me), 4.50(2H, s, CH₂Ar), 7.25–7.50(11H, m) | C H N | 67.10 5.63 9.39 | 66.81 5.44 9.46 | 66.96 5.42 9.50 |
| 95 | $C_{27}H_{29}N_3O_5$ (475) | 493(M⁺NH₄, 10%; 476, MH⁺, 16%; (DCI/NH₃) | CDCl₃ + CF₃CO₂D 1.30(3H, t, Me), 1.70–1.75(4H, m), 2.40–2.45(4H, m), 4.20(2H, q), 4.53(2H, s), 7.25–7.50(11H, m) | C H N | 68.20 6.15 8.84 | 68.13 5.95 8.88 | 68.28 6.00 8.91 |
| 96 | $C_{24}H_{24}N_2O_5$ | 421, MH⁺, 100% (DCI/NH₃) | CDCl₃ + CF₃CO₂D 1.88(4H, m), 2.50(2H, m), 3.77(3H, s), 4.04(2H, m), 7.00(2H, d, J=8Hz), 7.21(1H, s), 7.38–7.53(8H, m) | | | | |
| 97 | $C_{23}H_{22}N_2O_5$ | 424, MNH₄⁺, 2%; 407, MH⁺, 100%; | CDCl₃ + CF₃CO₂D 1.92(4H, m), | | | | |

TABLE 2-continued

| N° | Mol. Formula (M. Wt) | Mass spec m/z, mass, intensity (mode) | ¹H nmr Solvent δ all 400 MHz | Microanalysis Calc | Found | Infra-red cm⁻¹ |
|---|---|---|---|---|---|---|
| | | 291, 71% (DCI/NH₃) | 2.55(2H, m), 4.09(2H, m), 7.03(2H, d, J=8Hz), 7.24(1H, s), 7.29(1H, s), 7.39–7.55(7H, m) | | | |
| 98 | $C_{23}H_{26}N_3O_3Cl$ | 392, (M—Cl)⁺, 100% (ESI + QIMS) | d₆-DMSO 2.15(2H, m), 3.20(2H, m), 3.29(6H, s), 4.12(2H, m), 6.77(1H, s), 6.78(1H, s), 7.00(2H, d, J=8Hz), 7.32(1H, m), 7.40(2H, m), 7.55(4H, m), 10.13(2H, br.s) | | | |
| 99 | $C_{22}H_{24}N_3O_3Cl$ | 430, 7%; 412, 5%; 478, 100% | d₆-DMSO 2.85(6H, s, 2×Me), 3.50(2H, t, CH₂), 4.40(2H, t, CH₂), 6.75–7.55(11H, m), 10.15(2H, br.s, 2×NH), 10.75(1H, v.br.s., NH) | | | |
| 100 | $C_{26}H_{27}N_3O_6$ (477) | 495, M⁺NH₄, 13%; 478, MH⁺, 100%; 446, 15% (DCI/NH₃) | CDCl₃ + CF₃CO₂D 2.00–2.17(2H, m), 2.45–2.52(4H, m), 3.75(3H, s, Me), 3.88(3H, s, Me), 4.50(2H, s), 7.00–7.40(10H, m) | | | |
| 101 | $C_{20}H_{16}N_2O_5$ (364) | 382, M⁺NH₄, 80%; 365, M⁺+1, 100% (DCI/NH₃) | d₆-DMSO 4.70(2H, s, OCH₂), 6.75–7.55(11H, m), 10.12(1H, br.s., NH), 10.17(1H, br.s., NH) | | | |
| 102 | $C_{22}H_{23}N_3O_3$ (377) | 378, MH⁺, 100% (DCI/NH₃) | CDCl₃ + CF₃CO₂D 3.10(6H, s, 2×Me), 3.65(2H, t, CH₂), 4.40(2H, t, CH₂), 6.95–7.50(11H, m) | | | |
| 103 | $C_{19}H_{15}N_2O_3F$ (338) | 339 100% (DCI/NH₃) | CDCl₃ + CF₃CO₂D 3.91(3H, s), 7.03(2H, d), 7.16–7.30(4H, m), 7.39–7.48(4H, m) | C 67.45 H 4.47 N 8.28 | 67.44 4.37 8.27 | 67.44 4.32 8.29 |
| 104 | $C_{21}H_{19}N_3O_4$ (377) | 395, MNH⁺₄, 32%; 378, MH⁺, 38% (DCI/NH₃) | d₆-DMSO 2.04(3H, s), 4.51(2H, d), 5.18(1H, t,), 6.72(1H, s), 6.78(1H, s), 7.36(2H, d), 7.50(4H, m), 7.62(2H, d) | | | |

TABLE 2-continued

| N° | Mol. Formula (M. Wt) | Mass spec m/z, mass, intensity (mode) | $^1$H nmr Solvent δ all 400 MHz | Microanalysis | Calc | Found | Infra-red cm$^{-1}$ |
|---|---|---|---|---|---|---|---|
| 105 | $C_{19}H_{13}O_2N_3$ | 316, MH$^+$, 100%, 201, 53% (DCI/NH$_3$) | CDCl$_3$ + CF$_3$CO$_2$D 7.25(1H, s), 7.38(1H, s), 7.43–7.60(5H, m), 7.61(2H, d, J=7Hz), 7.85(2H, d, J=7Hz) | C H N | 72.37 4.16 13.33 | 72.26 4.21 13.21 | 72.15 4.20 13.16 |

We claim:

1. A compound selected from the group consisting of a diketopiperazine of formula (A):

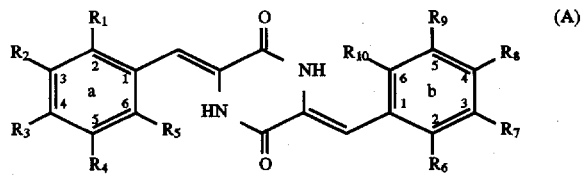

wherein $R_8$ is NHAc wherein Ac is acetyl; $R_1$ is H or halogen; $R_2$ is H; $R_3$ is halogen, $C_1$–$C_6$ alkoxy, —N($R^{11}R^{12}$) or —NHCOOR$^{13}$; and each of $R^{11}$ and $R^{12}$ is independently H or $C_1$–$C_6$ alkyl and $R^{13}$ is $C_1$–$C_6$ alkyl; $R_4$ is H; $R_5$ is halogen or CF$_3$; $R_6$, $R_7$, $R_9$ and $R_{10}$ are H; and the pharmaceutically acceptable salts thereof.

2. A compound selected from the group consisting of a diketopiperazine of formula (A):

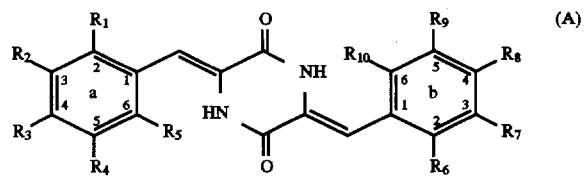

wherein $R_1$, $R_6$, $R_7$, $R_8$, $R_9$ and $R_{10}$ are H; $R_2$ is H and $R_3$ is —CH$_2$SR$^{11}$, —CH$_2$SCOR$^{11}$, —NHCO(CH$_2$)$_n$CO$_2$R$^{11}$, —O(CH$_2$)$_n$CO$_2$R$^{11}$, —O(CH$_2$)$_n$N(R$^{11}$R$^{12}$), or $R_2$ is —CH$_2$SCOR$^{13}$ or —CH$_2$SR$^{11}$ and each of R$^{11}$ and R$^{12}$ is independently H or $C_1$–$C_6$ alkyl and R$^{13}$ is $C_1$–$C_6$ alkyl; and $R_3$ is H; and $R_4$ and $R_5$ are both H or form, together with the carbon atoms to which they are attached, a benzene ring; and the pharmaceutically acceptable salts thereof.

3. A pharmaceutical or veterinary composition comprising a pharmaceutically or veterinarily acceptable carrier or diluent and, as an active principle, a compound as claimed in claim 1.

4. A pharmaceutical or veterinary composition comprising a pharmaceutically or veterinarily acceptable carrier or diluent and, as an active principle, a compound as claimed in claim 2.

* * * * *